(12) United States Patent
Carpenter et al.

(10) Patent No.: US 12,391,638 B2
(45) Date of Patent: Aug. 19, 2025

(54) HYDROFORMYLATION CATALYSTS COMPRISING FLUOROPHOSPHINE LIGANDS AND PRECURSORS THEREOF

(71) Applicant: ExxonMobil Chemical Patents Inc., Baytown, TX (US)

(72) Inventors: Alex E. Carpenter, Seabrook, TX (US); Danielle G. Singleton, Houston, TX (US); Sarah A. Kheir, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 321 days.

(21) Appl. No.: 17/906,843

(22) PCT Filed: Mar. 25, 2021

(86) PCT No.: PCT/US2021/024068
§ 371 (c)(1),
(2) Date: Sep. 20, 2022

(87) PCT Pub. No.: WO2021/202225
PCT Pub. Date: Oct. 7, 2021

(65) Prior Publication Data
US 2023/0159424 A1 May 25, 2023

Related U.S. Application Data

(60) Provisional application No. 63/003,600, filed on Apr. 1, 2020.

(51) Int. Cl.
*C07C 45/50* (2006.01)
*B01J 31/18* (2006.01)
*B01J 31/20* (2006.01)

(52) U.S. Cl.
CPC ......... *C07C 45/505* (2013.01); *B01J 31/1845* (2013.01); *B01J 31/20* (2013.01); *B01J 2231/321* (2013.01); *B01J 2531/0208* (2013.01); *B01J 2531/845* (2013.01)

(58) Field of Classification Search
CPC ..... C07C 45/505; B01J 31/1845; B01J 31/20; B01J 2231/321; B01J 2531/845
See application file for complete search history.

(56) References Cited

U.S. PATENT DOCUMENTS

| | | |
|---|---|---|
| 3,278,612 A | 10/1966 | Greene |
| 3,418,351 A | 12/1968 | Greene et al. |
| 3,624,158 A | 11/1971 | Deffner et al. |
| 4,070,403 A | 1/1978 | Homeier |
| 4,625,067 A | 11/1986 | Hanin |
| 5,237,105 A | 8/1993 | Summerlin |
| 2005/0119508 A1 | 6/2005 | Clausi et al. |

FOREIGN PATENT DOCUMENTS

| | | |
|---|---|---|
| EP | 3144073 A1 | 3/2017 |
| FR | 1389699 A | 2/1965 |
| GB | 1049291 A | 11/1966 |
| WO | 2021/202225 A1 | 10/2021 |

OTHER PUBLICATIONS

Brennessel, W. et al., (2002) "Bis (1, 2, 3, 4-η4-anthracene) cobaltate (1−)", Angewandte Chemie International Edition, vol. 41, No. 7, pp. 1211-1215.
Brennessel, W. et al., (2012) "Naphthalene and anthracene cobaltates (1−): useful storable sources of an atomic cobalt anion", Inorganic Chemistry, vol. 51, No. 16, pp. 9076-9094.
Carpenter, A. E. et al., (2013) "[1, 1-Co2 (CO) 6 (CNAr) 2]: A Structural Mimic of the Elusive D2d Isomer of [Co2 (CO) 8]", Chemistry—A European Journal, vol. 19, No. 32, pp. 10452-10457.
Ellis, J. E., (2006) "Adventures with substances containing metals in negative oxidation states", Inorganic chemistry, vol. 45, No. 8, pp. 3167-3186.
Hebrard, F. et al., (2009) "Cobalt-catalyzed hydroformylation of alkenes: generation and recycling of the carbonyl species, and catalytic cycle", Chemical Reviews, vol. 109, No. 9, pp. 4272-4282.
Kruck, T. et al., (1965) "Synthesis of Tetrakis(trifluorophosphine)cobalt Hydride and Hexakis(trifluorophosphine) tungsten(0) [1]", Angewandte Chemie International Edition in English, vol. 4, No. 2, pp. 148-149.
Kruck, T. et al., (1965) "Synthesis of Tetrakistrifluorophosphinoiridium Hydride and the Proton Magnetic Resonance Spectra of the Hydrides HM (PF3) 4 (M=Co, Rh, Ir)", Angewandte Chemie International Edition in English, vol. 4, No. 10, pp. 870-871.
Kruck, T. et al., (1967) "Trifluorophosphine complexes of transition metals", Angewandte Chemie International Edition in English, vol. 6, No. 1, , pp. 53-67.
International Preliminary Report on Patentability received for PCT Application No. PCT/US2021/024068, mailed on Oct. 13, 2022, 8 Pages.
International Search Report and Written Opinion received for PCT Application No. PCT/US2021/024068, mailed on Jul. 8, 2021, 12 Pages.
Saalfeld, F. E. et al., (1968) "Mass spectra of trifluorophosphinecarbonylcobalt hydrides", Journal of the American Chemical Society, vol. 90, No. 14, pp. 3684-3688.
Udovich, C. A et al., (1969) "Metal carbonyl-trifluorophosphine systems. VII. Cobalt carbonyl hydrides and perfluoroalkyls", Inorganic Chemistry, vol. 8, No. 4, pp. 938-944.
Zuidema, E. et al., (2007) "Electronic ligand effects on the regioselectivity of the rhodium-diphosphine-catalyzed hydroformylation of propene", Organometallics, vol. 26, No. 9, pp. 2234-2242.

*Primary Examiner* — Sikarl A Witherspoon

(57) ABSTRACT

This invention relates to a composition comprising a compound having a formula of $M_2(CO)_m(PF_3)_n$, wherein M is a group 9 metal (such as cobalt), m is 1, 2, 3, 4, 5, 6, or 7, n is 1, 2, 3, 4, 5, 6, or 7, and the sum of m and n is 8, that may be used as a hydroformylation pre¬catalyst for converting (such as hydroformylating) olefinic feeds, especially complex feeds comprising internal olefins and high degrees of branching.

39 Claims, 7 Drawing Sheets

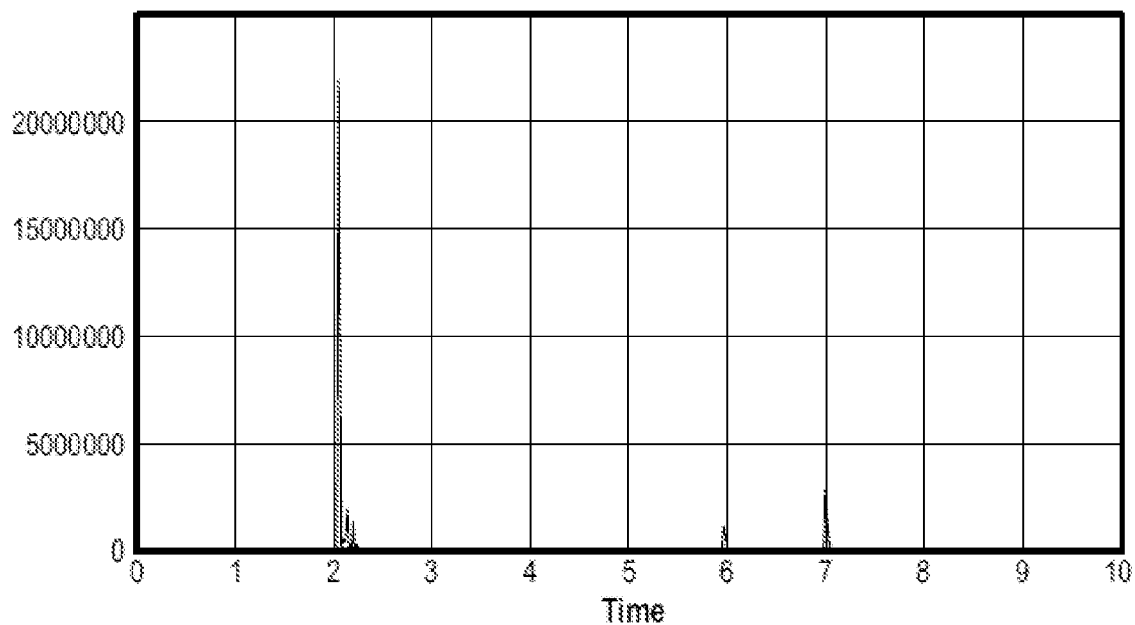
FIG. 8
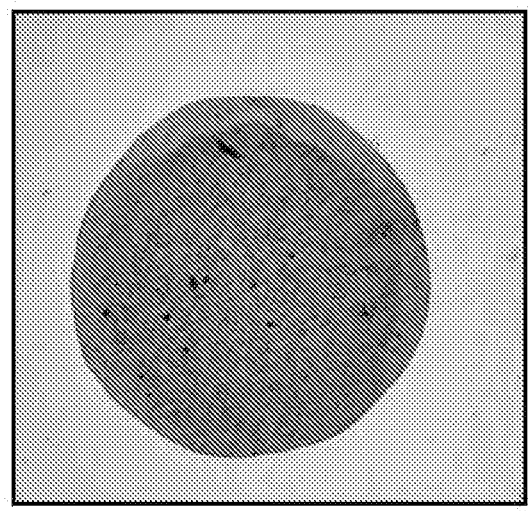 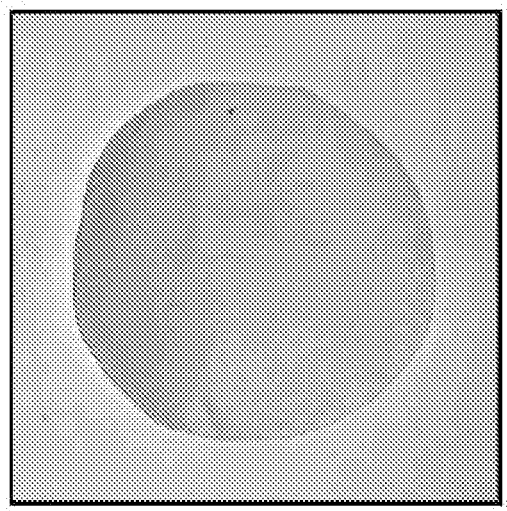
FIG. 9A  FIG. 9B

HYDROFORMYLATION CATALYSTS COMPRISING FLUOROPHOSPHINE LIGANDS AND PRECURSORS THEREOF

PRIORITY

This application is a National Phase Application claiming priority to PCT Application Serial No. PCT/US2021/024068 filed Mar. 25, 2021, which claims priority to U.S. Provisional Application No. 63/003,600 filed Apr. 1, 2020, the disclosure of the U.S. Provisional Application is incorporated by reference in its entirey.

FIELD

The present disclosure generally relates to hydroformylation and, more specifically, to group 9 metal complexes modified with one or more fluorophosphine ligands that may be effective for promoting hydroformylation under high syngas pressures.

BACKGROUND

Hydroformylation reactions form oxygenated organic compounds (such as aldehydes or alcohols) by reacting a mixture of carbon monoxide and hydrogen, such as synthesis gas ("syngas"), with one or more olefinic hydrocarbons in the presence of a hydroformylation catalyst. This process is commonly referred to as the Oxo Process. Typical hydroformylation catalysts include those based upon cobalt or rhodium chemistries. Generally, an initial reaction product formed following hydroformylation is an aldehyde having one more carbon atom in its molecular structure than does the olefinic hydrocarbon from which it was produced. The initially produced aldehyde following hydroformylation is oftentimes reduced through hydrogenation into the corresponding alcohol for ease of processing and further use. Alternately, oxidation to the corresponding carboxylic acid may be conducted.

For example, long-chain alcohols may be prepared through hydroformylation of the corresponding olefins, followed by reduction. Long-chain branched alcohols or functionalized products formed therefrom may find utility in a number of applications due to their amphiphilic character and biodegradability. Long-chain alcohols or functionalized products formed therefrom may find use as surfactants, emollients, lubricants, coatings, wetting agents, corrosion inhibitors, synthetic base stocks, and/or therapeutic delivery agents. Unfortunately, highly branched olefins often react poorly under typical hydroformylation reaction conditions.

Long-chain, substantially unbranched alcohols may be prepared with certain hydroformylation catalysts using a starting material bearing vinyl termination upon the carbon chain, such as a linear alpha olefin or linear alpha olefin oligomer. Conversion of the vinyl olefin moiety into an alcohol moiety through hydroformylation and subsequent reduction usually preserves the linearity or branchiness of the carbon chain without introducing new chain branches and results in the alcohol moiety being located at or near the terminus of the carbon chain.

Hydridocobalt carbonyl compounds, such as $HCo(CO)_4$, are used as hydroformylation catalysts in many instances. The inherent volatility of $HCo(CO)_4$ allows it to be recovered using stripping gasses, as described in U.S. Pat. Nos. 4,625,067 and 5,237,105. One issue associated with the use of $HCo(CO)_4$ in hydroformylation is cobalt plating as a result of the inherent instability of $HCo(CO)_4$ in the absence of high CO partial pressures. Phosphine modification of hydridocobalt carbonyl compounds has been attempted for altering their catalytic performance and for promoting improved handling. U.S. Pat. No. 4,070,403 describes the use of $HCo(CO)_4$ modified with phosphine ligands for conducting hydroformylation reactions. Other references employing phosphine modification of hydridocobalt carbonyl hydroformylation catalysts include U.S. Pat. Nos. 3,624,158; 3,418,351; 3,278,612; and French Patent 1389699. A common theme among phosphine-modified hydroformylation catalyst systems has been a drive to lower pressure process conditions and achieving a greater selectivity for linear products. This adds greatly to catalyst complexity, reduces tolerance of the catalyst system to complex/branched feeds, and decreases the attendant volatility of the catalyst system.

As mentioned above, $HCo(CO)_4$ tends to decompose in the absence of high carbon monoxide pressures. In addition, this hydroformylation catalyst oftentimes produces excessive paraffinic and heavy byproducts. As a result, high syngas pressures are often used during cobalt-mediated hydroformylation reactions. Phosphine modification of $HCo(CO)_4$ with conventional phosphine ligands for alteration of the catalytic properties may be problematic in this respect, however, due to the propensity of conventional phosphine ligands to undergo displacement with carbon monoxide, especially under high syngas pressures. In addition, phosphine modification tends to decrease the volatility of the parent $HCo(CO)_4$ compound, thereby making recycling of the catalyst considerably more difficult than when phosphine modification is not employed.

Trifluorophosphine-modified hydridocobalt complexes are isolable due to the high affinity of the $PF_3$ ligand for cobalt and exhibit far greater thermal stability than other phosphine-modified hydridocobalt complexes as a result. Use of these types of phosphine-modified cobalt complexes in hydroformylation is presently unknown. References of interest describing isolated trifluorophosphine-modified hydridocobalt complexes include Hebrard, F. et al. (2009) "Cobalt-Catalyzed Hydroformylation of Alkenes: Generation and Recycling of the Carbonyl Species, and Catalytic Cycle," *Chem. Rev.*, v.109(9), pp. 4272-4282; Frenz, B. A. (1970) *Inorg. Chem.*, v.9, pp. 2403-2407; Kruck, T. et al. (1965) *Angew. Chem. Int. Ed.*, v.4, p. 148; Kruck, T. (1965) et al., *Angew. Chem. Int. Ed.*, v.4 p. 870; and Kruck, T. (1967) *Angew. Chem. Int. Ed.*, v.6, pp. 53-67.

Additional references of interest include: Carpenter, A. E. et al. (2013) "[1,1-$Co_2(CO)_6(CNAr^{Mes2})_2$]: A Structural Mimic of the Elusive $D_{2d}$ Isomer of [$Co_2(CO)_8$]," *Chem. Eur. J.*, v.19, pp. 10452-10457.

SUMMARY

This invention relates to compounds and compositions comprising a compound having a formula of: $M_2(CO)_m(PF_3)_n$, wherein M is a group 9 metal, m is 1, 2, 3, 4, 5, 6, or 7, n is 1, 2, 3, 4, 5, 6, or 7, and the sum of m and n is 8.

This invention also relates to catalyst systems comprising the reaction product of hydrogen and a compound having a formula of: $M_2(CO)_m(PF_3)_n$, wherein M is a group 9 metal, m is 1, 2, 3, 4, 5, 6, or 7, n is 1, 2, 3, 4, 5, 6, or 7, and the sum of m and n is 8.

Also provided herein are methods comprising contacting an olefinic hydrocarbon with carbon monoxide and hydrogen, such as syngas, and a precatalyst comprising a reaction product of $M_2(CO)_m$ with $(PF_3)$, wherein M is a group 9 metal, m is 1, 2, 3, 4, 5, 6, or 7, (such as $Co_2(CO)_8$ and $PF_3$)

under conditions effective to convert the olefinic hydrocarbon into a hydroformylation reaction product.

Other methods provided herein comprise forming an active hydroformylation catalyst having a formula of HCo(CO)$_{m'}$(PF$_3$)$_{n'}$ under conditions effective to convert an olefinic hydrocarbon into a hydroformylation reaction product, wherein m' is 1, 2, or 3, n' is 1, 2, or 3, and the sum of m' and n' is 4; and contacting the olefinic hydrocarbon with the active hydroformylation catalyst and syngas under the conditions effective to convert the olefinic hydrocarbon into the hydroformylation reaction product.

Further, this invention relates to recovering the hydroformylation catalyst or a spent form thereof and conveying the recovered catalyst to an upstream location for recycle/reuse.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and having the benefit of this disclosure.

FIGS. 6-8 show illustrative gas chromatographs of the hydroformylation reaction products obtained from Entries 1-3 in Example 2, respectively.

FIGS. 9A and 9B shows images of plating residue incurred using conventional hydroformylation catalysts (FIG. 10A) versus the plating residue incurred using Co$_2$(CO)$_4$(PF$_3$)$_4$(FIG. 10B).

DETAILED DESCRIPTION

Figure 1:
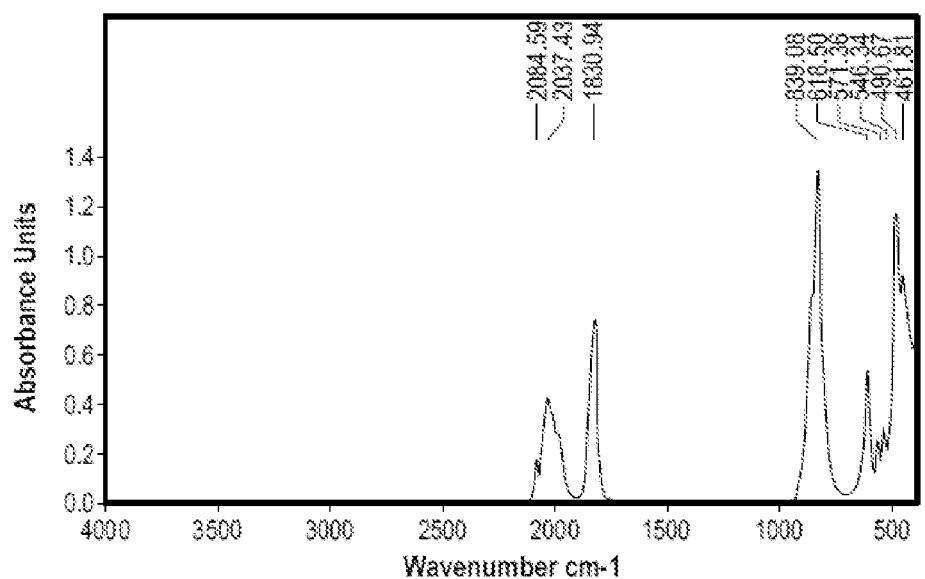
FIG. 1 shows an attenuated total reflectance (ATR) Fourier transform infrared (FTIR) spectrum of the reaction product of Example 1.

The present disclosure relates generally to hydroformylation and, more specifically, to hydroformylation catalyst precursors and catalyst systems comprising trifluorophosphine-modified group 9 metal complexes and methods for hydroformylation therewith.

There are presently issues associated with phosphine modification of hydridocobalt carbonyl complexes for conducting hydroformylation. In particular, phosphine modification may limit volatility of the catalyst for facilitating recycling. In addition, conventional phosphines may be readily displaced by carbon monoxide under high syngas pressures. As such, it is relatively difficult at present to modify the catalytic properties and other performance characteristics of hydridocobalt carbonyl compounds, particularly under elevated CO partial pressures where phosphine ligands are typically readily displaced.

The present disclosure provides trifluorophosphine-modified group 9 metal complexes that may be effectively converted into an active hydroformylation catalyst under hydroformylation reaction conditions. Advantageously, the active hydroformylation catalysts may retain significant volatility to promote recycling thereof and afford a different product distribution than do conventional phosphine-modified hydridocobalt carbonyl compounds. While not wishing to be bound by theory, it is thought that these advantageous properties result from retention of at least one trifluorophosphine ligand in the active hydroformylation catalyst. In particular, the active hydroformylation catalysts produced according to the disclosure herein may convert an olefinic hydrocarbon into a hydroformylation reaction product with a higher degree of branching than is typically attainable with conventional phosphine-modified hydroformylation catalysts. Further, the active hydroformylation catalysts disclosed herein may avoid the detrimental effects of cobalt plating that commonly occur with unmodified hydridocobalt carbonyl complexes, which may facilitate relatively simple catalyst recycling processes. With a decreased incidence of cobalt plating, considerably less plant downtime may be realized compared to unmodified hydridocobalt carbonyl complexes.

Advantageously, the active hydroformylation catalysts disclosed herein may be formed in situ under hydroformylation reaction conditions from readily produced trifluorophosphine-modified dimeric group 9 metal complexes, particularly under high syngas pressures of about 1,000 psi or above. Due to the strong bonding between the cobalt center and the trifluorophosphine ligand(s), the trifluorophosphine ligand(s) is/are believed to be retained in the active hydroformylation catalyst to afford particularly advantageous properties, such as tolerance toward both linear and branched olefin feeds and low propensity toward cobalt plating. Further advantageously, the dimeric group 9 metal complexes disclosed herein are liquids and may be used under similar conditions to those employed for liquid hydridocobalt carbonyl complexes in hydroformylation reactions. More particular disclosure regarding the dimeric group 9 metal complexes and the active hydroformylation catalysts formed therefrom follows herein below.

Additional process advantages may also be realized with trifluorophosphine-modified hydroformylation catalysts. As described in U.S. Patent Application Publication U.S. 2005/0119508, the Cobalt Flash Process requires use of a secondary cobalt recovery following vapor-phase recovery of volatile cobalt carbonyls (e.g., HCo(CO)$_4$/Co$_2$(CO)$_8$) in a stripper reactor. In part, oxidative aqueous recovery is necessary due to the propensity for HCo(CO)$_4$ to decompose into cobalt metal and less volatile cobalt containing compounds. The high binding affinity of cobalt for trifluorophosphine in conjunction with the enhanced stability of trifluorophosphine-containing cobalt compounds enables the optional use of stripper reactor(s) to remove cobalt from crude hydroformylation product streams in the disclosure herein. Thus, trifluorophosphine-modified cobalt hydroformylation catalysts may be recovered using stripper reactor(s) with enhanced efficiency relative to HCo(CO)$_4$.

Definitions

All numerical values within the detailed description and the claims herein are modified by "about" or "approximately" with respect to the indicated value, and take into account experimental error and variations that would be expected by a person having ordinary skill in the art. Unless otherwise indicated, room temperature is about 23° C.

As used in the present disclosure and claims, the singular forms "a," "an," and "the" include plural forms unless the context clearly dictates otherwise.

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides). Under this scheme, Co, Rh, Ir, and Mt are group 9 transition metals.

The terms "group," "radical," and "substituent" may be used interchangeably herein.

Reference to a group without specifying a particular isomer thereof (e.g., butyl) expressly discloses all isomers (e.g., n-butyl, iso-butyl, sec-butyl, tert-butyl and cyclobutyl), unless otherwise indicated.

The term "hydrocarbon" refers to a class of compounds having hydrogen bound to carbon, and encompasses saturated hydrocarbon compounds, unsaturated hydrocarbon compounds, and mixtures of hydrocarbon compounds (saturated and/or unsaturated), including mixtures of hydrocarbon compounds having different numbers of carbon atoms. The term "$C_n$" refers to hydrocarbon(s) or a hydrocarbyl group having n carbon atom(s) per molecule or group, wherein n is a positive integer. Such hydrocarbon compounds may be one or more of linear, branched, cyclic, acyclic, saturated, unsaturated, aliphatic, or aromatic. As used herein, a cyclic hydrocarbon may be referred to as "carbocyclic," which includes saturated, unsaturated, and partially unsaturated carbocyclic compounds, as well as aromatic carbocyclic compounds. The term "heterocyclic" refers to a carbocyclic ring containing at least one ring heteroatom.

The terms "hydrocarbyl radical," "hydrocarbyl group," or "hydrocarbyl" may be used interchangeably and are defined to mean a group consisting of hydrogen and carbon atoms only and bearing at least one unfilled valence position when removed from a parent compound. A hydrocarbyl group can be saturated or unsaturated, linear or branched, cyclic or acyclic, aromatic or non-aromatic. Preferred hydrocarbyls include $C_1$-$C_{100}$ radicals that may be linear or branched. Examples of such radicals include, but are not limited to, alkyl groups such as methyl, ethyl, n-propyl, isopropyl, n-butyl, isobutyl, sec-butyl, tert-butyl, pentyl, iso-amyl (isopentyl), hexyl, octyl cyclopropyl, cyclobutyl, cyclopentyl, cyclohexyl, cyclooctyl, and the like. The term "hydrocarbyl group having 1 to about 100 carbon atoms" refers to a moiety selected from a linear, cyclic or branched $C_1$-$C_{100}$ hydrocarbyl group.

The term "optionally substituted" means that a group may be unsubstituted or substituted. For example, the term "optionally substituted hydrocarbyl" refers to replacement of at least one hydrogen atom or carbon atom in a hydrocarbyl group with a heteroatom or heteroatom functional group. Unless otherwise specified, any of the hydrocarbyl groups herein may be optionally substituted.

The terms "linear" or "linear hydrocarbon" refer to a hydrocarbon or hydrocarbyl group having a continuous carbon chain without side chain branching.

The terms "branched" or "branched hydrocarbon" refer to a hydrocarbon or hydrocarbyl group having a linear carbon chain or a carbocyclic ring, in which a hydrocarbyl side chain extends from the linear carbon chain or the carbocyclic ring.

The terms "saturated" or "saturated hydrocarbon" refer to a hydrocarbon or hydrocarbyl group in which all carbon atoms are bonded to four other atoms, with the exception of an unfilled valence position being present upon carbon in a hydrocarbyl group.

The terms "unsaturated" or "unsaturated hydrocarbon" refer to a hydrocarbon or hydrocarbyl group in which one or more carbon atoms are bonded to less than four other atoms, exclusive of an open valence position upon carbon being present. That is, the term "unsaturated" refers to a hydrocarbon or hydrocarbyl group bearing one or more double and/or triple bonds, with the double and/or triple bonds being between two carbon atoms and/or between a carbon atom and a heteroatom.

The terms "alkyl radical," and "alkyl" are used interchangeably throughout the present disclosure and refer to a hydrocarbyl group having no unsaturated carbon-carbon bonds, and which may be optionally substituted. An alkyl group can be linear, branched, cyclic, or a combination thereof. "Alkyl radicals" are defined to be $C_1$-$C_{100}$ alkyls that may be linear, branched, or cyclic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like. Substituted alkyl radicals are radicals in which at least one hydrogen atom of the alkyl radical has been substituted with at least a non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SiR*, —SiR*$_3$, —GeR*, —GeR*$_3$, —SnR*, —SnR*$_3$, —PbR*$_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring.

The term "branched alkyl" means that an alkyl group contains a tertiary or quaternary carbon (a tertiary carbon is a carbon atom bound to three other carbon atoms; a quaternary carbon is a carbon atom bound to four other carbon atoms). For example, 3,5,5 trimethylhexylphenyl is an alkyl group (hexyl) having three methyl branches (hence, one tertiary and one quaternary carbon) and thus is a branched alkyl bound to a phenyl group.

The terms "cycloalkyl" or "cycloalkyl group" interchangeably refer to a saturated hydrocarbyl group wherein the carbon atoms form one or more ring structures. The terms "cycloalkenyl" or "cycloalkenyl group" interchangeably refer to a cyclic hydrocarbyl group comprising a carbon-carbon double bond in the ring.

The terms "alkene" and "olefin" are used synonymously herein. Similarly, the terms "alkenic" and "olefinic" are used synonymously herein. Unless otherwise noted, all possible geometric isomers are encompassed by these terms. The term "alkenyl" refers to a hydrocarbyl group having a carbon-carbon double bond. Alkenyl groups may be straight-chain, branched-chain, or cyclic and contain one or more carbon-carbon double bonds. Alkenyl radicals may be optionally substituted. Examples of alkenyls can include ethenyl, propenyl, allyl, 1,4-butadienyl, cyclopropenyl, cyclobutenyl, cyclopentenyl, cyclohexenyl, cyclooctenyl and the like.

The term "arylalkenyl" refers to an aryl group where a hydrogen atom has been replaced with an alkenyl or substituted alkenyl group. For example, styryl indenyl is an indene substituted with an arylalkenyl group (a styrene group).

The carbon-carbon double bond in an alkene may be in various structural or geometric isomer forms, which may include vinylidenes, vinyls, disubstituted vinylenes and trisubstituted vinylenes.

The term "vinyl" (also referred to as a "vinyl olefin") refers to an olefin represented by the following formula

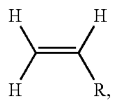

wherein R is a hydrocarbyl group, preferably a saturated hydrocarbyl group such as an alkyl group.

The term "vinylidene" (also referred to as a "vinylidene olefin") refers to an olefin represented by the following formula

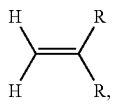

wherein each R is an independently selected hydrocarbyl group, preferably a saturated hydrocarbyl group such as an alkyl group. Vinylidenes are 1,1-disubstituted vinylene groups.

The term "disubstituted vinylene" (also referred to as a "disubstituted vinylidene olefin") refers to
(i) an olefin represented by the following formula

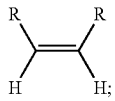

(ii) an olefin represented by the following formula

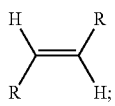

or
(iii) a mixture thereof in any proportion,
wherein each R is an independently a hydrocarbyl group, preferably a saturated hydrocarbyl group such as an alkyl group. The term "disubstituted vinylene" is not inclusive of the term "vinylidene." That is, disubstituted vinylenes represent only 1,2-disubstituted vinylene groups and do not include vinylidene groups.

The term "trisubstituted vinylene" (also referred to as a "trisubstituted olefin") refers to an olefin represented by the following formula

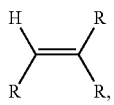

wherein each R is an independently a hydrocarbyl group, preferably a saturated hydrocarbyl group such as an alkyl group. Alternatively, two R groups on adjacent carbon atoms may together form a non-aromatic ring structure, with a third R group remaining as a pendant hydrocarbyl group.

The term "tetrasubstituted olefin" refers to an olefin represented by the following formula

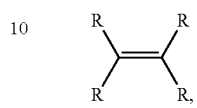

wherein each R is an independently a hydrocarbyl group, preferably a saturated hydrocarbyl group such as an alkyl group. Alternatively, two R groups on adjacent carbon atoms may together form a non-aromatic ring structure.

The term "alpha olefin" refers to an olefin having a terminal carbon-carbon double bond in the structure thereof (R"HC=CH$_2$, where R" is hydrogen or a hydrocarbyl group; preferably R" is an alkyl group). Non-limiting examples of alpha olefins include, for instance, ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornene. Any of these alpha olefins may undergo hydroformylation in the disclosure herein.

In the present disclosure, ethylene shall be considered an alpha olefin.

A "polymer" has two or more of the same or different mer units. A "homopolymer" is a polymer having mer units that are the same. A "copolymer" is a polymer having two or more mer units that are different from each other. An oligomer is typically a polymer (homo- or co-polymer) having from 2 to 100 mer units. "Different" as used to refer to mer units indicates that the mer units differ from each other by at least one atom or are different isomerically.

Hydroformylation Catalysts

Active hydroformylation catalysts of the present disclosure may be formed from a catalyst precursor (also referred to as a precatalyst) comprising the reaction product of Co$_2$(CO)$_8$ and PF$_3$, which is preferably a compound having Formula 1:

$$M_2(CO)_m(PF_3)_n \qquad \text{Formula 1}$$

wherein each M is a group 9 metal (such as Co or Rh), m is 1, 2, 3, 4, 5, 6, or 7, n is 1, 2, 3, 4, 5, 6, or 7, and the sum of m and n is 8. Preferably, M is cobalt. Preferably, m is 2 or greater. In particular, m may be 2, 3, 4, 5, 6, or 7 and n may be 1, 2, 3, 4, 5, or 6. More preferably, both m and n are 4. Any single dimeric group 9 metal complex or mixture of dimeric group 9 metal complexes may be present in the compositions disclosed herein, wherein the dimeric group 9 metal complexes may be bridged by carbon monoxide ligands or contain a direct metal-metal bond.

Certain dimeric group 9 metal complexes disclosed herein are believed to contain one or more bridging carbon monoxide groups (ligands), in addition to other non-bridging ligands. In particular, bridged dimeric group 9 metal complexes of the present disclosure are believed to comprise two bridging carbon monoxide groups, each between a first metal center and a second metal center, preferably between a first cobalt center and a second cobalt center. In a particular example, the dimeric group 9 metal complexes of the present disclosure may have a structure represented by Formula 2

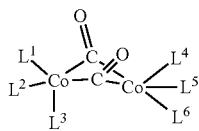

Formula 2 wherein $L^1$, $L^2$, $L^3$, $L^4$, $L^5$, and $L^6$ are independently CO or $PF_3$, provided that at least one of $L^1$, $L^2$ and $L^3$ is CO, at least one of $L^4$, $L^5$ and $L^6$ is CO, and at least one of $L^1$, $L^2$, $L^3$, $L^4$, $L^5$, and $L^6$ is $PF_3$. Preferably at least one of $L^1$-$L^6$ is $PF_3$ and any of $L^1$-$L^6$ that are not $PF_3$ are instead CO. Particular dimeric group 9 metal complexes defined by Formula 2 may include:
  a) at least one of $L^1$-$L^6$ is CO, and any of $L^1$-$L^6$ that are not CO are $PF_3$, provided that at least one of $L^1$-$L^6$ is $PF_3$;
  b) at least two of $L^1$-$L^6$ are CO, and any of $L^1$-$L^6$ that are not CO are $PF_3$, provided that at least one of $L^1$-$L^6$ is $PF_3$;
  c) at least three of $L^1$-$L^6$ are CO, and any of $L^1$-$L^6$ that are not CO are $PF_3$, provided that at least one of $L^1$-$L^6$ is $PF_3$;
  d) at least four of $L^1$-$L^6$ are CO, and any of $L^1$-$L^6$ that are not CO are $PF_3$, provided that at least one of $L^1$-$L^6$ is $PF_3$;
  e) five of $L^1$-$L^6$ are CO, and one of $L^1$-$L^6$ is $PF_3$;
  f) one of $L^1$, $L^2$ and $L^3$ is CO, and any of $L^1$-$L^6$ that are not CO are $PF_3$, provided that at least one of $L^1$-$L^6$ is $PF_3$;
  g) two of $L^1$, $L^2$ and $L^3$ are CO, and any of $L^1$-$L^6$ that are not CO are $PF_3$, provided that at least one of $L^1$-$L^6$ is $PF_3$;
  h) three of $L^1$, $L^2$ and $L^3$ are CO, and any of $L^1$-$L^6$ that are not CO are $PF_3$, provided that at least one of $L^1$-$L^6$ is $PF_3$;
  i) at least one of $L^1$, $L^2$ and $L^3$ is CO, at least one of $L^4$, $L^5$ and $L^6$ is CO, and any of $L^1$-$L^6$ that are not CO are $PF_3$, provided that at least one of $L^1$-$L^6$ is $PF_3$;
  j) at least two of $L^1$, $L^2$ and $L^3$ are CO, at least one of $L^4$, $L^5$ and $L^6$ is CO, and any of $L^1$-$L^6$ that are not CO are $PF_3$, provided that at least one of $L^1$-$L^6$ is $PF_3$;
  k) at least two of $L^1$, $L^2$ and $L^3$ are CO, at least two of $L^4$, $L^5$ and $L^6$ are CO, and any of $L^1$-$L^6$ that are not CO are $PF_3$, provided that at least one of $L^1$-$L^6$ is $PF_3$;
  l) each of $L^1$, $L^2$ and $L^3$ is CO, at least one of $L^4$, $L^5$ and $L^6$ is CO, and any of $L^4$-$L^6$ that are not CO are $PF_3$, provided that at least one of $L^4$-$L^6$ is $PF_3$; and
  m) $L^1$, $L^2$ and $L^3$ are each CO, two of $L^4$, $L^5$ and $L^6$ are CO, and one of $L^4$-$L^6$ is $PF_3$.

The compounds represented by Formula 2 may be in a fused square pyramid geometry about each cobalt center. In the dimeric group 9 metal complexes represented by Formula 2, any of the CO groups and any of the $PF_3$ groups may be located in an axial position and/or in an equatorial position, which may rapidly fluctuate between isomeric positions, such as described for other cobalt carbonyl complexes in Carpenter, A. E. et al. (2013) "[1,1-$Co_2(CO)_6$(CNAr$^{Mes_2}$)$_2$]: A Structural Mimic of the Elusive $D_{2d}$ Isomer of [$Co_2(CO)_8$]," *Chem. Eur. J.*, v.19, pp. 10452-10457.

In another particular example, the dimeric group 9 metal complexes of the present disclosure may comprise one or more metal-bridged structures represented by Formulas 3A and 3B below,

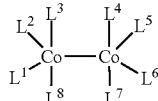

Formula 3A

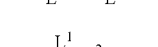

Formula 3B wherein, $L^1$, $L^2$, $L^3$, $L^4$, $L^5$, $L^6$, $L^7$, and $L^8$ are independently CO or $PF_3$, and at least one of $L^1$-$L^8$ is $PF_3$ and any of $L_1$-$L_8$ that are not $PF_3$ are CO. These group 9 metal complexes may be characterized by a trigonal bipyramidal or distorted trigonal bipyramidal geometry about the cobalt centers. In the dimeric group 9 metal complexes represented by Formulas 3A and 3B any of the CO groups and any of the $PF_3$ groups may be located in an axial position and/or in an equatorial position. Particular dimeric group 9 metal complexes defined by Formulas 3A and 3B may include:
  a) at least one of $L^1$-$L^8$ is CO, and any of $L^1$-$L^8$ that are not CO are $PF_3$, provided that at least one of $L^1$-$L^8$ is $PF_3$;
  b) at least two of $L^1$-$L^8$ are CO, and any of $L^1$-$L^8$ that are not CO are $PF_3$, provided that at least one of $L^1$-$L^8$ is $PF_3$;
  c) at least three of $L^1$-$L^8$ are CO, and any of $L^1$-$L^8$ that are not CO are $PF_3$, provided that at least one of $L^1$-$L^8$ is $PF_3$;
  d) at least four of $L^1$-$L^8$ are CO, and any of $L^1$-$L^8$ that are not CO are $PF_3$, provided that at least one of $L^1$-$L^8$ is $PF_3$;
  e) at least five of $L^1$-$L^8$ are CO, and any of $L^1$-$L^8$ that are not CO are $PF_3$, provided that at least one of $L^1$-$L^8$ is $PF_3$;
  f) at least six of $L^1$-$L^8$ are CO, and any of $L^1$-$L^8$ that are not CO are $PF_3$, provided that at least one of $L^1$-$L^8$ is $PF_3$;
  g) seven of $L^1$-$L^8$ are CO, and one $L^1$-$L^8$ that are not CO are $PF_3$;
  h) one of $L^1$-$L^3$ and $L^8$ is CO, and any of $L^1$-$L^8$ that are not CO are $PF_3$, provided that at least one of $L^1$-$L^8$ is $PF_3$;
  i) two of $L^1$-$L^3$ and $L^8$ are CO, and any of $L^1$-$L^8$ that are not CO are $PF_3$, provided that at least one of $L^1$-$L^8$ is $PF_3$;
  j) three of $L^1$-$L^3$ and $L^8$ are CO, and any of $L^1$-$L^8$ that are not CO are $PF_3$, provided that at least one of $L^1$-$L^8$ is $PF_3$;
  k) $L^1$-$L^3$ and $L^8$ are CO, and any of $L^4$-$L^7$ that are not CO are $PF_3$, provided that at least one of $L^4$-$L^7$ is $PF_3$;
  l) at least one of $L^1$, $L^2$, $L^3$, and $L^8$ is CO, at least one of $L^4$-$L^7$ is CO, and any of $L^1$-$L^8$ that are not CO are $PF_3$, provided that at least one of $L^1$-$L^8$ is $PF_3$;
  m) at least two of $L^1$, $L^2$, $L^3$, and $L^8$ are CO, at least one of $L^4$-$L^7$ is CO, and any of $L^1$-$L^8$ that are not CO are $PF_3$, provided that at least one of $L^1$-$L^8$ is $PF_3$;

n) at least two of $L^1$, $L^2$, $L^3$, and $L^8$ are CO, at least two of $L^4$-$L^7$ are CO, and any of $L^1$-$L^8$ that are not CO are $PF_3$, provided that at least one of $L^1$-$L^8$ is $PF_3$;
o) at least three of $L^1$, $L^2$, $L^3$, and $L^8$ are CO, at least one of $L^4$-$L^7$ are CO, and any of $L^1$-$L^8$ that are not CO are $PF_3$, provided that at least one of $L^1$-$L^8$ is $PF_3$;
p) at least three of $L^1$, $L^2$, $L^3$, and $L^8$ are CO, at least two of $L^4$-$L^7$ are CO, and any of $L^1$-$L^8$ that are not CO are $PF_3$, provided that at least one of $L^1$-$L^8$ is $PF_3$;
q) at least three of $L^1$, $L^2$, $L^3$, and $L^8$ are CO, at least three of $L^4$-$L^7$ are CO, and any of $L^1$-$L^8$ that are not CO are $PF_3$, provided that at least one of $L^1$-$L^8$ is $PF_3$;
r) $L^1$, $L^2$, $L^3$, and $L^8$ are each CO, at least one of $L^4$-$L^7$ is CO, and any of $L^4$-$L^7$ that are not CO are $PF_3$, provided that at least one of $L^1$-$L^8$ is $PF_3$;
s) $L^1$, $L^2$, $L^3$, and $L^8$ are each CO, at least two of $L^4$-$L^7$ are CO, and any of $L^4$-$L^7$ that are not CO are $PF_3$, provided that at least one of $L^1$-$L^8$ is $PF_3$; and
t) $L^1$, $L^2$, $L^3$, and $L^8$ are each CO, three of $L^4$-$L^7$ are CO, and one of $L^4$-$L^7$ is $PF_3$.

Referring again to Formulas 1, 2, 3A, and 3B, combinations applicable to variables m and n include the following m,n pairs: 7,1; 6,2; 5,3; 4,4; 3,5; 2,6; and 7,1. In particular examples applicable to Formulas 1 and 2, m and n are each 4, in which case two of $L^1$, $L_2$ and $L_3$ may be $PF_3$ and one of $L^1$, $L_2$ and $L_3$ may be CO, and two of $L_4$, $L_5$ and $L_6$ may be $PF_3$ and one of $L_4$, $L_5$ and $L_6$ may be CO.

This invention also relates to a catalyst system comprising the reaction product of hydrogen and one or more compounds represented by 1, 2, 3A, and 3B and any variations thereof described herein. Preferably, the catalyst systems comprise the reaction product of hydrogen and a compound having a formula of: $M_2(CO)_m(PF_3)_n$, wherein M is a group 9 metal (preferably M is Co), m is 1, 2, 3, 4, 5, 6, or 7, n is 1, 2, 3, 4, 5, 6, or 7, and the sum of m and n is 8. Hydrogen may be provided to the catalyst system as hydrogen gas, as syngas, or any other hydrogen source that provides hydrogen to react with the pre-catalyst compound(s).

The hydrogen and precatalyst compound are typically combined at ratios where at least one equivalent of hydrogen is provided for every pre-catalyst molecule. Preferably, a large excess of hydrogen is utilized (i.e., 10, 100, 1000, 10,0000, 100,000, 100,000,000 equivalents).

Preferably, under hydroformylation reaction conditions, the dimeric group 9 metal complexes of the present disclosure are converted into an active catalytic species (active hydroformylation catalyst) and facilitate conversion of an olefinic feed into a hydroformylation reaction product. The active catalytic species may represent a reaction product of the dimeric group 9 metal complex and hydrogen (such as from syngas). While not wishing to be bound by theory, it is believed that the active catalytic species formed under the hydroformylation reaction conditions may be represented by Formula 4

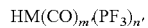

Formula 4 wherein M is the group 9 metal, m' is 1, 2, or 3, n' is 1, 2, or 3, and the sum of m' and n' is 4. Preferably, M is cobalt. Preferably, m' is 1 or greater. In particular, m' is 1 or 2 and or n' is 1 or 2. More preferably, both m' and n' are 2.

Combinations applicable to variables m' and n' in Formula 4 include the following m',n' pairs: 3,1; 2,2; and 1,3. The carbon monoxide and $PF_3$ groups may be in any available axial or equatorial position about the metal center.

The dimeric group 9 metal complexes of the present disclosure are effective precatalysts for forming a catalyst system as described herein (optionally in situ under hydroformylation reaction conditions), where the catalyst system exhibits improved stability (e.g., does not decompose) at CO partial pressures of less than 1,500 psig (10 MPa), such as less than 1,000 psig (6.9 MPa), relative to the cobalt catalyst system of hydrogen plus $HCo(CO)_4$ under the same hydroformylation reaction conditions. Alternately, the catalyst system is stable at temperatures of 80° C. or more (such as 100° C. or more). Alternately, the catalyst system is stable (e.g., does not decompose) at temperatures of 100° C. or more (such as 120° C. or more) and CO partial pressures of less than 1,500 psig (10 MPa), such as less than 1,000 psig (6.9 MPa). By "does not decompose" is meant that the metal compound in the catalyst system, such as a cobalt compound, does not afford substantial quantities of group 9 metal (such as cobalt) precipitates ("metal plating") during a hydroformylation reaction as indicated by particulates (e.g., group 9 metal (such as cobalt) particulates) isolable by filtration of the product. Preferably, the catalyst systems described herein do not produce hydroformylation reaction product having more group 9 metal (such as cobalt) precipitates per gram than a catalyst system consisting essentially of the reaction product of $HCo(CO)_4$ and hydrogen (hereinafter "reference catalyst system") produces per gram, when tested under the same hydroformylation reaction conditions). Preferably, the catalyst systems described produce less (such as 10% less, or 20% or less, or 50% less, or 70% less, or 80% less, or 90% less, or 95% less, or 99% less) group 9 metal (such as cobalt) precipitates per gram than the reference catalyst system (defined above) when tested under the same hydroformylation reaction conditions. For avoidance of doubt, reactant feed ratios are considered part of the reaction conditions.

Preferably, the catalyst systems formed herein are liquid at temperatures of 10° C. or more (such as 20° C. or more, such as 30° C. or more). Preferably, the catalyst systems formed herein are liquid at CO partial pressures of 6.9 MPa or more, alternately 10 MPA or more. Preferably, the catalyst systems formed herein are liquid at temperatures of 100° C. or more (such as 110° C. or more, such as 120° C. or more) and CO partial pressures of 6.9 MPa or more, alternately 10 MPA or more.

Preferably, the catalyst systems described herein do not decompose at CO partial pressures of less than 10 MPa.

Preferably, the catalyst systems described herein are stable at temperatures of 80° C. or more and CO partial pressures of less than 10 MPa.

Preferably, the catalyst systems described herein are liquid at temperatures of 10° C. or more, and optionally at CO partial pressures of 6.9 MPa or more.

As referenced above, the dimeric group 9 metal complexes of the present disclosure are effective precatalysts for forming an active catalytic species in situ under hydroformylation reaction conditions. As used herein, the term "hydroformylation" refers to the combined process of introducing an aldehyde moiety to an olefinic hydrocarbon and subsequently reducing the aldehyde moiety to a primary alcohol moiety. To distinguish between the two process operations herein, the non-reduced (aldehyde) reaction product produced initially may be referred to in the present disclosure as the "hydroformylation reaction product," and the reduced (alcohol) reaction product may be referred to herein as a "reduced hydroformylation reaction product."

Accordingly, hydroformylation methods of the present disclosure may comprise contacting an olefinic hydrocarbon with syngas and a precatalyst comprising a reaction product of $Co_2(CO)_8$ and $PF_3$ under conditions effective to convert the olefinic hydrocarbon into a hydroformylation reaction product. The reaction product of $Co_2(CO)_8$ and $PF_3$ may have a structure represented by Formula 1, Formula 2, or Formulas 3a/3b in more specific examples, wherein the variables associated with these formulas are described above. Thus, in more specific examples, hydroformylation methods of the present disclosure featuring in situ catalyst generation may comprise contacting an olefinic hydrocarbon with syngas and a precatalyst comprising a compound having Formula 1, wherein M, m and n are defined as above, and converting the olefinic hydrocarbon into a hydroformylation reaction product under the conditions effective to convert the olefinic hydrocarbon into the hydroformylation reaction product.

Conditions effective to convert the olefinic hydrocarbon into the hydroformylation reaction product in the present disclosure may comprise a combined hydrogen and carbon monoxide partial pressure of at least about 1,000 psig (6.9 MPa) or at least about 1,500 psig (10 MPa), preferably the conditions comprise a syngas partial pressure of partial pressure of at least about 1,000 psig (6.9 MPa) or at least about 1,500 psig (10 MPa). The hydroformylation methods may further comprise forming an active hydroformylation catalyst comprising a compound having Formula 4 under the conditions effective to convert the olefinic hydrocarbon into the hydroformylation reaction product, wherein M, m' and n' are as defined as above for Formula 4.

Alternately, hydroformylation methods of the present disclosure may comprise forming an active hydroformylation catalyst having Formula 4 under conditions effective to convert an olefinic hydrocarbon into a hydroformylation reaction product, wherein the variables are defined as above.

Suitable olefinic hydrocarbons that may undergo hydroformylation according to the disclosure herein are represented by Formula 5 below.

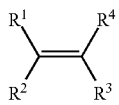

Formula 5

In Formula 5, $R^1$, $R^2$, $R^3$, and $R^4$ may be independently selected from hydrogen or a $C_1$-$C_{30}$ linear or branched hydrocarbyl group, which may be optionally substituted.

Suitable olefinic hydrocarbons may be an alpha olefin or an internal olefinic hydrocarbon, either of which may be linear or branched. In addition, suitable olefinic hydrocarbons may have one or multiple carbon-carbon double bonds. One suitable type of olefinic feed that may undergo hydroformylation according to the disclosure herein may comprise a mixture of various olefinic hydrocarbon isomers (such as one or more propylene oligomers). More specifically, such olefinic feeds may represent a mixture comprising two or more of an alpha olefin, a vinylidene olefin, a vinyl olefin, a trisubstituted olefin, a tetrasubstituted olefin, or any combination thereof.

Non-limiting examples of alpha olefins that may undergo hydroformylation according to the disclosure herein include, for instance, ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornene, or any combination thereof. Polyalphaolefins comprising any of these alpha olefins or any combination thereof (such as olimomers thereof) may also contain a double bond that may undergo hydroformylation according to the disclosure herein.

A suitable olefinic feed may also comprise an oligomerization reaction product of a lower olefin (e.g., $C_2$ to $C_{30}$, such as $C_3$ to $C_{12}$), such as propylene, wherein a plurality of branched olefinic products may be present. For example, a suitable olefinic feed may comprise one or more of a $C_2$, $C_3$, or $C_4$ olefin oligomer. The term "oligomer" refers to a molecule having a 2 to 100 (such as 2 to 20, such as 3 to 10) repeating monomer units. Illustrative oligomers include dimers, trimers, tetramers, pentamers, and hexamers, and mixtures thereof. In particular, oligomers (typically oligomers containing 2 to 12 mer units, such as 3, 4, 5, or 6 mer units) of $C_2$ to $C_{20}$ olefins, such as ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, are useful herein. A commercially available olefinic feed suitable for use in the disclosure herein is a composition comprising highly branched higher olefins sold by ExxonMobil Chemical Company (Houston, Texas) under the name TETRAMER K™, which comprises a high concentration of isomeric $C_{12}$ olefins.

An olefinic hydrocarbon may be contacted with a precatalyst of the present disclosure according to Scheme 1 below, wherein a branched or unbranched aldehyde may be formed, depending upon the region-selectivity achieved for introducing the carbonyl group. Branching already present in the olefinic hydrocarbon may be preserved in the hydroformylation process.

Scheme 1

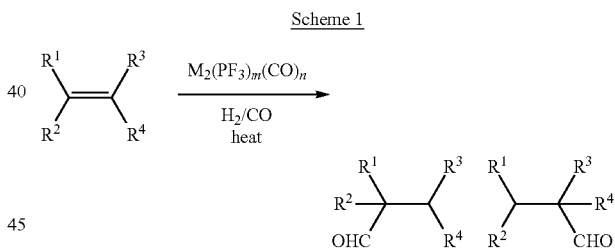

where $R^1$, $R^2$, $R^3$ and $R^4$ are H or hydrocarbyl, M is a group 9 metal, m is 1, 2, 3, 4, 5, 6, or 7, and n is 1, 2, 3, 4, 5, 6 or 7.

Effective amounts of the precatalyst disclosed herein for performing hydroformylation may range from about 150 µmol precatalyst/mol olefin feed to about 8,000 µmol precatalyst/mol olefin feed, or about 100 ppm metal to about 5,000 ppm metal (where ppm is defined as mg of metal per kg of olefin feed, preferably wherein the metal is cobalt). Loading may depend on the complexity of the substrate. For example, a lower loading may be used for lighter alpha olefins, while more challenging substrates may employ a higher catalyst loading. In one or more embodiments, the precatalyst loading may be about 2,400 µmol precatalyst/mol olefin feed or about 1,500 ppm. Under conditions effective to promote hydroformylation, the precatalyst may be converted into an active hydroformylation catalyst bearing at least one $PF_3$ ligand. The active hydroformylation catalyst generated in situ may then facilitate the conversion of an olefinic hydrocarbon into a hydroformylation reaction product. Conditions effective to convert the olefinic hydrocarbon into the hydroformylation reaction product may comprise a syngas pressure of at least about 1,000 psig (~7 MPa) or at least about 1,500 psig (~10 MPa). Suitable ranges include from about 1,000 psig (~7 MPa) to about 2,000 psig (~13.8 MPa), from about 1,250 psig (~8.6 MPa) to about 1,500 psig (~10 MPa), from about 1,500 psig (~10 MPa) to about 1,750 psig (~12 MPa), or from about 1,500 psig (~10 MPa) to about 2,000 psig (~13.8 MPa). Conditions effective to convert the olefinic hydrocarbon may further comprise a temperature of about 100° C. to about 200° C., which includes from about 125° C. to about 175° C., from about 125° C. to about 200° C., and from about 100° C. to about 175° C. In one example embodiment, a temperature of about 150° C. may be used to form the active hydroformylation catalyst and conduct hydroformylation. Reaction times under these conditions may range from about 0.5 hours to about 96 hours. Optionally, additional $PF_3$ may be introduced into the reactor to control the number of $PF_3$ ligands bound to the active hydroformylation catalyst. Both batch wise and continuous reaction conditions may be employed for generating hydroformylation reaction products according to the disclosure herein. For continuous reaction conditions, any of continuously stirred tank reactors, plug flow reactors or loop reactors may be used. Solvents or diluents are not necessary when conducting the hydroformylation reaction according to the disclosure herein. When used, suitable solvents or diluents may include, but are not limited to, alkane solvents, polar protic solvents, polar aprotic solvents, chlorinated solvents, and aromatic solvents. In a particular example, up to about 10 wt. % water may be added to control byproduct formation under the hydroformylation reaction conditions. Without being bound by theory or mechanism, water may hinder the formation of aldol condensates and other heavy reaction products.

The diversity and complexity of the hydroformylation reaction product formed according to the disclosure herein may depend on the diversity and complexity of the olefinic hydrocarbon from which it was formed. Depending on the regioisomeric position at which the carbonyl group is introduced, the hydroformylation reaction product may be linear or branched. Any branching already present it the olefinic hydrocarbon may be preserved when undergoing hydroformylation according to the disclosure herein. Thus, in any embodiment, a hydroformylation reaction product may comprise a mixture of isomers varying in size, branching, and aldehyde location (i.e., at a terminal or non-terminal location of the carbon backbone). Based on their relative rates of formation, hydroformylation reaction products of the present disclosure may comprise a mixture of aldehydes exhibiting an average of about 1.2 branches per aldehyde molecule up to about 2 branches per aldehyde molecule, which may be exceeded if additional branches are present in the olefin prior to hydroformylation and/or are introduced during hydroformylation.

Conversion selectivity of an olefinic feed to a hydroformylation reaction product may depend on the complexity of the olefinic feed. Advantageously, when compared to other phosphine-modified cobalt complexes, the precatalysts disclosed herein may promote hydroformylation of alpha olefins with a high selectivity for branched aldehydes. For example, the ratio of linear aldehydes to branched aldehydes may be less than or equal to about 2, such as from about 0.9 to about 2, though a ratio lower than 0.9 may be attainable. Additionally, the precatalysts disclosed herein may convert alpha olefins to product at a higher conversion rate than do other phosphine-modified cobalt complexes. For example, an olefinic feed comprising alpha olefins may be converted to a hydroformylation reaction product comprising from about 85 mol. % to about 99 mol. %, preferably about 90 mol. % to about 95 mol. % aldehyde molecules. In contrast, a hydroformylation reaction product generated using an unmodified cobalt complex (i.e., $Co(CO)_8$) may generate a lower percentage of aldehyde and a higher amount of alcohol and/or paraffin byproducts.

In a more complex olefinic feed, for example, an olefinic feed comprising a variety of linear and branched olefin isomers, conversion of the olefinic feed to aldehydes, alcohols, and $C_{n+1}$ paraffins (where n is the average number of carbons per olefin molecule) may be lower, such as from about 15 mol. % to about 25 mol. %. This conversion is surprising and significant, considering that phosphine-modified ligands typically exhibit poor performance on complex feeds of these types. Percent conversion may be calculated in any embodiment of the disclosure herein according to the following equation:

$$\% \text{ conversion} = \frac{\text{aldehydes+alcohols} + C_{n+1} \text{ paraffins}}{\text{aldehydes+alcohols} + C_{n+1} \text{ paraffins+olefin feed}}.$$

In industrial applications, it may be desirable to recover the hydroformylation catalyst for recycling and reuse, which may require separation of the hydroformylation catalyst from the hydroformylation reaction product. Whereas conventional phosphine ligands impede catalyst volatility and make catalyst recycling more difficult (e.g., by utilizing complex catalyst recycle loops with multi-phase extraction or other costly methods), the precatalyst disclosed herein offer access to active hydroformylation catalysts that are phosphine-modified and remain amenable to vapor-phase catalyst recovery. Thus, the methods disclosed herein may further comprise recovering the hydroformylation catalyst or a spent form thereof (such as by vapor phase recovery, typically with CO, syngas, hydrogen, or nitrogen used as a stripping gas) and conveying the recovered catalyst to an upstream location for reuse. The stripping gas typically entrains the group 9 metal compounds (such as volatile group compounds, such as volatile cobalt compounds) in the stripping gas such that the metal compounds can be removed (such as by being are taken out overhead).

Optionally, a hydroformylation reaction product may be further converted into a reduced hydroformylation reaction product by subjecting the hydroformylation reaction product to reducing conditions, such as through catalytic hydrogenation of the aldehyde carbonyl group. Accordingly, some hydroformylation methods of the present disclosure may comprise providing an olefinic feed comprising an olefinic hydrocarbon, contacting the olefin hydrocarbon with a precatalyst comprising a compound having a formula of $M_2(CO)_m(PF_3)_n$ (where M, m, and n are as previously set forth above) under conditions effective to convert the olefinic hydrocarbon into a hydroformylation reaction product, and reducing the hydroformylation reaction product to generate a reduced hydroformylation reaction product. Reduction may take place through catalytic hydrogenation in many instances. Suitable hydrogenation catalysts and hydrogenation conditions will be familiar to one having ordinary skill in the art. Exemplary hydrogenation conditions and catalysts are provided hereinafter.

Reducing may comprise exposing the hydroformylation reaction product to hydrogen and a hydrogenation catalyst (i.e., catalytic hydrogenation conditions using a catalyst comprising Fe, Co, Ni, Ru, Rh, Pd, Os, Ir, or Pt, preferably supported on an inorganic substrate, and a hydrogen partial pressure of, for example, about 5 MPa to about 20 MPa, and a reaction temperature up to about 180° C.). Alternately, reducing may be conducted using a hydride reducing agent, such as sodium borohydride. Catalytic hydrogenation may remove any residual carbon-carbon unsaturation present in the hydroformylation reaction product, as well as reduce at least a portion of the aldehyde groups into primary alcohols. Hydride reduction, either conducted alone or in combination with catalytic hydrogenation, may complete the reduction of the aldehyde moieties into a primary alcohol moiety in the reduced hydroformylation reaction product. In an example process configuration, reduction may comprise exposing the hydroformylation reaction product to catalytic hydrogenation followed by a sodium borohydride reduction to produce a reduced hydroformylation reaction product.

The diversity and complexity of the reduced hydroformylation reaction product may depend on the diversity and complexity of the hydroformylation reaction product upon which reduction is performed. Thus, in any embodiment, a reduced hydroformylation reaction product may comprise a mixture of isomers varying in size, branching, and alcohol location (i.e., at a terminal or non-terminal position of the carbon backbone). As used herein, the term "carbon backbone" refers to the longest series of covalently bonded carbon atoms that create the continuous chain of the hydrocarbon molecule. Optionally, a reduced hydroformylation reaction product may be further processed, for example, by distillation, to isolate particularly desirable fractions, such as $C_{13}$ alcohols. A reduced hydroformylation reaction product generated from hydroformylation and subsequent reduction of a complex olefinic feed may be particularly valuable in the manufacture of detergents as a non-limiting example.

Although when compared to unmodified hydridocobalt carbonyl complexes, the trifluorophosphine-modified cobalt complexes disclosed herein may exhibit a lower conversion efficiency, avoidance of cobalt plating using the trifluorophosphine-modified cobalt complexes of the present disclosure is predicted to offset that lowered efficiency.

The present disclosure relates to the following non-limiting embodiments.

A. Compositions comprising a trifluorophosphine-modified metal carbonyl compound. The compositions comprise: a compound having a formula of:

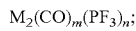

wherein M is a group 9 metal, m and n are independently 1, 2, 3, 4, 5, 6, or 7, and the sum of m and n is 8.

B. Hydroformylation methods. The methods comprise: contacting an olefinic hydrocarbon with syngas and a pre-catalyst comprising a reaction product of $Co_2(CO)_8$ and $PF_3$ under conditions effective to convert the olefinic hydrocarbon into a hydroformylation reaction product.

C. Hydroformylation methods using a precatalyst. The methods comprise: forming an active hydroformylation catalyst having a formula of:

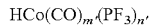

under conditions effective to convert an olefinic hydrocarbon into a hydroformylation reaction product; wherein m' and n' are integers, a sum of m' and n' is 4; and contacting the olefinic hydrocarbon with the active hydroformylation catalyst and syngas under the conditions effective to convert the olefinic hydrocarbon into the hydroformylation reaction product.

Embodiments A-C may have one or more of the following elements in any combination:

Element 1: wherein M is cobalt.

Element 2: wherein m is 2, 3, 4, 5, 6, or 7.

Element 3: wherein the compound has two bridging carbon monoxide groups each between a first metal center and a second metal center.

Element 4: wherein the compound has a structure represented by the formula

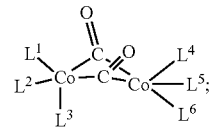

wherein at least one of $L^1$, $L^2$ and $L^3$ is CO, at least one of $L^4$, $L^5$ and $L^6$ is CO, and any of $L^1$-$L^6$ that are not CO are $PF_3$, at least one $PF_3$ being present.

Element 5: wherein m and n are each 4.

Element 6: wherein two of $L^1$, $L^2$, $L^3$, and $L^7$ are $PF_3$ and one of $L^1$, $L^2$, $L^3$, and $L^7$ is CO, and two of $L^4$, $L^5$, $L^6$, and $L^8$ are $PF_3$ and one of $L^4$, $L^5$, $L^6$, and $L^8$ is CO.

Element 7: wherein the compound has a structure represented by one or more of the following formulas

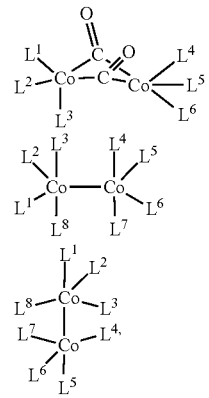

wherein, if the compound is carbonyl bridged, at least one of $L^1$-$L^6$ is $PF_3$ and any of $L^1$-$L^6$ that are not $PF_3$ are CO, and if the compound has a cobalt-cobalt bond, at least one of $L^1$-$L^8$ is $PF_3$ and any of $L_1$-$L_8$ that are not $PF_3$ are CO.

Element 8: wherein the reaction product of $Co_2(CO)_8$ and $PF_3$ comprises a compound having a formula of

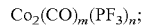

wherein m and n are independently 1, 2, 3, 4, 5, 6, or 7, and a sum of m and n is 8.

Element 9: wherein the method further comprises forming an active hydroformylation catalyst comprising a compound having a formula of

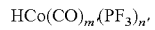

from the reaction product under the conditions effective to convert the olefinic hydrocarbon into the hydroformylation reaction product; wherein m' and n' are independently 1, 2 or 3, a sum of m' and n' is 4'.

Element 10: wherein the method further comprises converting the hydroformylation reaction product into a reduced hydroformylation reaction product by hydrogenating the hydroformylation reaction product.

Element 11: wherein the conditions effective to convert the olefinic hydrocarbon into the hydroformylation reaction product comprise a syngas pressure of at least about 1,000 psig (6.9 MPa).

Element 12: wherein m' is 2 or 3.

Element 13: wherein m' and n' are each 2.

Element 14: wherein the olefinic hydrocarbon comprises an alpha olefin.

Element 15: wherein the hydroformylation reaction product is characterized by a ratio of linear aldehydes to branched aldehydes of about 0.9 to about 2.

Element 16: wherein the olefinic hydrocarbon comprises an alpha olefin, a vinylidene olefin, a vinyl olefin, a trisubstituted olefin, a tetrasubstituted olefin, or any combination thereof.

Element 17: wherein the olefinic hydrocarbon comprises one or more propylene oligomers.

Element 18: wherein the active hydroformylation catalyst is formed under the conditions effective to convert the olefinic hydrocarbon into the hydroformylation reaction product from a precatalyst comprising a compound having a formula of

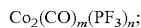

wherein m and n are independently 1, 2, 3, 4, 5, 6, or 7, and a sum of m and n is 8.

Element 19: wherein the conditions effective to convert the olefinic hydrocarbon into the hydroformylation reaction product comprise a syngas pressure of at least about 1,000 psig (6.9 MPa).

Element 20: wherein the method further comprises converting the hydroformylation reaction product into a reduced hydroformylation reaction product by hydrogenating the hydroformylation reaction product.

Element 21: wherein m' is 1, 2 or 3.

Element 22: wherein m' and n' are each 2.

Element 23: wherein the olefinic hydrocarbon comprises an alpha olefin.

Element 24: wherein the hydroformylation reaction product is characterized by a ratio of linear aldehydes to branched aldehydes of about 0.9 to about 2.

Element 25: wherein the olefinic hydrocarbon comprises an alpha olefin, a vinylidene olefin, a vinyl olefin, a trisubstituted olefin, a tetrasubstituted olefin, or any combination thereof.

Element 26: wherein the olefinic hydrocarbon comprises one or more propylene oligomers.

By way of non-limiting example, illustrative combinations applicable to A include, but are not limited to: 1 and 2; 1-3; 1 and 3; 1, 4 and 5; 1 and 4-6; 1, 2 and 7; 2 and 3; 2 and 4; 2, 4 and 5; 2 and 6; 2 and 7; 3 and 4; 3-5; 3-6; 3 and 7; 4 and 5; and 4-6. Illustrative combinations applicable to B include, but are not limited to, 9 and 10; 9 and 11; 9 and 12; 9 and 13; 9 and 14; 9 and 15; 9 and 16; 9 and 17; 10 and 11; 10 and 12; 10 and 13; 10 and 14; 10 and 15; 10 and 16; 10 and 17; 11 and 12; 11 and 13; 11 and 14; 11 and 15; 11 and 16; and 11 and 17. Illustrative combinations applicable to C include, but are not limited to, 18 and 19; 18 and 20; 18 and 21; 18 and 22; 18 and 23; 18 and 24; 18 and 25; 18 and 26; 19 and 20; 19 and 23; 19 and 24; 19 and 25; 19 and 26; 20 and 23; 20 and 24; 20 and 25; and 20 and 26.

The present disclosure further relates to:

1. A composition comprising a compound having a formula of:

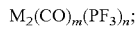

wherein M is a group 9 metal, m is 1, 2, 3, 4, 5, 6, or 7, n is 1, 2, 3, 4, 5, 6, or 7, and the sum of m and n is 8.

2. The composition of paragraph 1, wherein M is cobalt.

3. The composition of paragraph 1 or 2, wherein m is 2, 3, 4, 5, 6, or 7.

4. The composition of any one of paragraphs 1-3, wherein the compound has two bridging carbon monoxide groups each between a first metal center and a second metal center.

5. The composition of any one of paragraphs 1-4, wherein the compound is represented by the formula

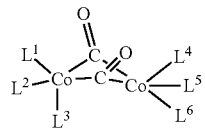

wherein $L^1$, $L^2$, $L^3$, $L^4$, $L^5$, and $L^6$ are independently CO or $PF_3$, provided that at least one of $L^1$, $L^2$ and $L^3$ is CO, at least one of $L^4$, $L^5$ and $L^6$ is CO, and at least one of $L^1$, $L^2$, $L^3$, $L^4$, $L^5$, and $L^6$ is $PF_3$.

6. The composition of any one of paragraphs 1-4, wherein m and n are each 4.

7. The composition of paragraph 5, wherein at least two of $L^1$, $L^2$, $L^3$, and $L^7$ are $PF_3$ and at least one of $L^1$, $L^2$, $L^3$, and $L^7$ is CO, and at least two of $L^4$, $L^5$, $L^6$, and $L^8$ are $PF_3$ and at least one of $L^4$, $L^5$, $L^6$, and $L^8$ is CO.

8. The composition of paragraph 1, wherein the compound is represented by one or more of the following formulas:

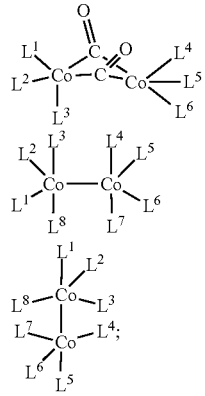

wherein, $L^1$, $L^2$, $L^3$, $L^4$, $L^5$, $L^6$, $L^7$, and $L^8$ are independently CO or $PF_3$, and if the compound is carbonyl bridged, at least one of $L^1$-$L^6$ is $PF_3$, any of $L^1$-$L^6$ that are not $PF_3$ are CO, and if the compound has a cobalt-cobalt bond, at least one of $L^1$-$L^8$ is $PF_3$ and any of $L_1$-$L_8$ that are not $PF_3$ are CO.

9. The composition of paragraph 1 wherein M is Rh.

10. A catalyst system comprising the reaction product of the compound of any of the above paragraphs 1 to 9 and hydrogen.

11. The catalyst system of paragraph 10, wherein the catalyst system does not decompose at CO partial pressures of less than 10 MPa.

12. The catalyst system of paragraph 10, wherein the catalyst system does not produce hydroformylation reaction product having more group 9 metal precipitates per gram than a catalyst system consisting essentially of the reaction product of $HCo(CO)_4$ and hydrogen produces per gram, when tested under the same hydroformylation reaction conditions.

13. The catalyst system of paragraph 10, wherein the catalyst system is stable at temperatures of 80° C. or more and CO partial pressures of less than 10 MPa.

14. The catalyst system of paragraph 10, wherein the catalyst system is liquid at temperatures of 10° C. or more, and optionally at CO partial pressures of 6.9 MPa or more.

15. A method comprising contacting an olefinic hydrocarbon with the catalyst system of any of paragraphs 10 to 14 under conditions effective to convert the olefinic hydrocarbon into a hydroformylation reaction product.

16. A method comprising: contacting an olefinic hydrocarbon with the composition of any of paragraphs 1 to 9, hydrogen, and an oxygen source under conditions effective to convert the olefinic hydrocarbon into a hydroformylation reaction product.

17. A method comprising: contacting an olefinic hydrocarbon with a hydrogen source and a precatalyst comprising the reaction product of $Co_2(CO)_8$ and $PF_3$ under conditions effective to convert the olefinic hydrocarbon into a hydroformylation reaction product.

18. A method comprising: contacting an olefinic hydrocarbon with a hydrogen source, an oxygen source, and a precatalyst comprising the reaction product of $Co_2(CO)_8$ and $PF_3$ under conditions effective to convert the olefinic hydrocarbon into a hydroformylation reaction product.

19. The method of paragraph 17 or 18 wherein the precatalyst is a composition of any of paragraphs 1 to 14.

20. The method of paragraph 17 or 18, further comprising:
forming an active hydroformylation catalyst comprising a compound represented by the formula of

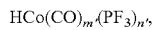

$HCo(CO)_{m'}(PF_3)_{n'}$;

from the reaction product under the conditions effective to convert the olefinic hydrocarbon into the hydroformylation reaction product; wherein m' is 1, 2, or 3, n' is 1, 2, or 3 and the sum of m' and n' is 4.

21. The method of any one of paragraphs 15 to 20, further comprising converting the hydroformylation reaction product into a reduced hydroformylation reaction product by hydrogenating the hydroformylation reaction product.

22. The method of any one of paragraphs 15-20, wherein the conditions effective to convert the olefinic hydrocarbon into the hydroformylation reaction product comprise a combined H and O partial pressure of at least about 6.9 MPa.

23. The method of any one of paragraphs 15-20, wherein the conditions effective to convert the olefinic hydrocarbon into the hydroformylation reaction product comprise a combined H and CO partial pressure of at least about 6.9 MPa.

24. The method of any one of paragraphs 20 to 23, wherein m' is 2 or 3.

25. The method of any one of paragraphs 20 to 23, wherein m' and n' are each 2.

26. The method of any one of paragraphs 15-25, wherein the olefinic hydrocarbon comprises an alpha olefin.

27. The method of paragraph 26, wherein the hydroformylation reaction product has a ratio of linear aldehydes to branched aldehydes of about 0.9 to about 2.

28. The method of any one of paragraphs 15-25, wherein the olefinic hydrocarbon comprises an alpha olefin, a vinylidene olefin, a vinyl olefin, a trisubstituted olefin, a tetrasubstituted olefin, or any combination thereof.

29. The method of any one of paragraphs 15-17, wherein the olefinic hydrocarbon comprises one or more propylene oligomers.

30. A method comprising: forming an active hydroformylation catalyst represented by the formula:

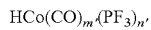

$HCo(CO)_{m'}(PF_3)_{n'}$ under conditions effective to convert an olefinic hydrocarbon into a hydroformylation reaction product; wherein m' is 1, 2, or 3, n' is 1, 2, or 3, and m'+n' is 4; and contacting the olefinic hydrocarbon with the active hydroformylation catalyst and syngas under the conditions effective to convert the olefinic hydrocarbon into the hydroformylation reaction product.

31. The method of paragraph 30, wherein the active hydroformylation catalyst is formed under the conditions effective to convert the olefinic hydrocarbon into the hydroformylation reaction product from a precatalyst comprising a compound represented by the formula of $Co_2(CO)_m(PF_3)_n$;

wherein m is 1, 2, 3, 4, 5, 6, or 7, n is 1, 2, 3, 4, 5, 6, or 7, and the sum of m and n is 8.

32. The method of paragraph 30 or paragraph 31, wherein the conditions effective to convert the olefinic hydrocarbon into the hydroformylation reaction product comprise a syngas pressure of at least about 6.9 MPa.

33. The method of any one of paragraphs 30 to 32, further comprising: converting the hydroformylation reaction product into a reduced hydroformylation reaction product by hydrogenating the hydroformylation reaction product.

34. The method of any one of paragraphs 30 to 33, wherein m' is 1, 2 or 3.

35. The method of any one of paragraphs 30 to 33, wherein m' and n' are each 2.

36. The method of any one of paragraphs 30 to 35, wherein the olefinic hydrocarbon comprises an alpha olefin.

37. The method of paragraph 36, wherein the hydroformylation reaction product has a ratio of linear aldehydes to branched aldehydes of about 0.9 to about 2.

38. The method of any one of paragraphs 30-35, wherein the olefinic hydrocarbon comprises an alpha olefin, a vinylidene olefin, a vinyl olefin, a trisubstituted olefin, a tetrasubstituted olefin, or any combination thereof.

39. The method of any one of paragraphs 30-35, wherein the olefinic hydrocarbon comprises one or more propylene oligomers.

40. The method of paragraph 15 to 39, further comprising recovering the hydroformylation catalyst or a spent form thereof and conveying the recovered catalyst to an upstream location for reuse.

41. The method of paragraph 40 wherein the hydroformylation catalyst or a spent form thereof is recovered by vapor phase recovery.

42. The method of paragraph 41 wherein the vapor phase recovery utilizes CO, syngas, hydrogen, or nitrogen as a stripping gas.

To facilitate a better understanding of the embodiments of the present disclosure, the following examples of preferred or representative embodiments are given. In no way should the following examples be read to limit, or to define, the scope of the disclosure.

EXAMPLES

Unless otherwise stated, materials were handled using standard glovebox and Schlenk techniques. All potentially air-sensitive materials were manipulated under dry nitrogen gas. Reagent grade starting materials were purchased from commercial venders and used as received or purified according to standard procedures. Anhydrous solvents were purchased from commercial sources and stored over activated 3 Å molecular sieves following standard procedures for drying and degassing. NMR data were recorded on Bruker 400

MHz and 500 MHz NMR Spectrometers. $^{13}C\{^1H\}$ chemical shifts are reported in ppm relative to SiMe$_4$ ($^{13}C\{^1H\}$ δ=0.0 ppm). $^{31}P$ NMR chemical shifts are reported relative to H$_3$PO$_4$ at δ=0.0 ppm and $^{19}F$ NMR chemical shifts are reported relative to trifluoroacetic acid at δ=−76.55 ppm. Attenuated total reflectance (ATR) Fourier transform infrared (FTIR) data were recorded on a Bruker Alpha IR instrument using a single-bounce Diamond ATR crystal.

A high-pressure, C-276 alloy autoclave reactor (250 mL) equipped with supervisory control and data acquisition capabilities was utilized for conducting hydroformylation reactions. The interior of the reactor was fitted with a glass liner. In a typical experiment, an olefinic feed (60 mL) was introduced to the reactor through an air-free injection port connected to a feed storage vessel. Agitation was initiated and the reactor was brought to a specified process temperature and a syngas pressure 100 psig (690 KPa) less than a specified process pressure (1:1 v/v H$_2$:CO). The reaction mixture was allowed to stir for 10 minutes to equilibrate. A solution (20 mL) of the specified catalyst was then delivered through an injection port on the autoclave. Syngas was utilized to drive the catalyst injection while simultaneously bringing the unit to the specified process pressure. The process pressure was maintained with syngas throughout the reaction and metered through a mass flow controller. At the end of the run, the syngas supply was halted, and the unit was de-pressurized and purged with nitrogen. Once cool, the reactor was opened and the liquid hydrocarbon product was transferred to a sample container for off-line product analysis.

Example 1: Precatalyst Preparation and Characterization. Co$_2$(CO)$_8$ (10 g, 29.42 mmol) was dissolved in toluene (50 mL). The resulting solution was transferred to a glass-lined autoclave fitted with magnetic stir bar. The autoclave was then sealed, pressurized with PF$_3$ (150 psig (1 MPa), and allowed to react for 16 hours at 30° C. Thereafter, the autoclave was depressurized, and the reaction mixture transferred to a round bottom flask where it was placed under reduced pressure (~200 mtorr (26.6 Pa)) for 5 hours to remove residual solvent and other volatile components. A dense, red/brown liquid (~10 mL) was obtained. The reaction product was characterized by ATR-FTIR spectroscopy and $^{13}C\{^1H\}$ NMR, $^{31}P\{^1H\}$ NMR, and $^{19}F$ NMR spectroscopy.

Figure 2:
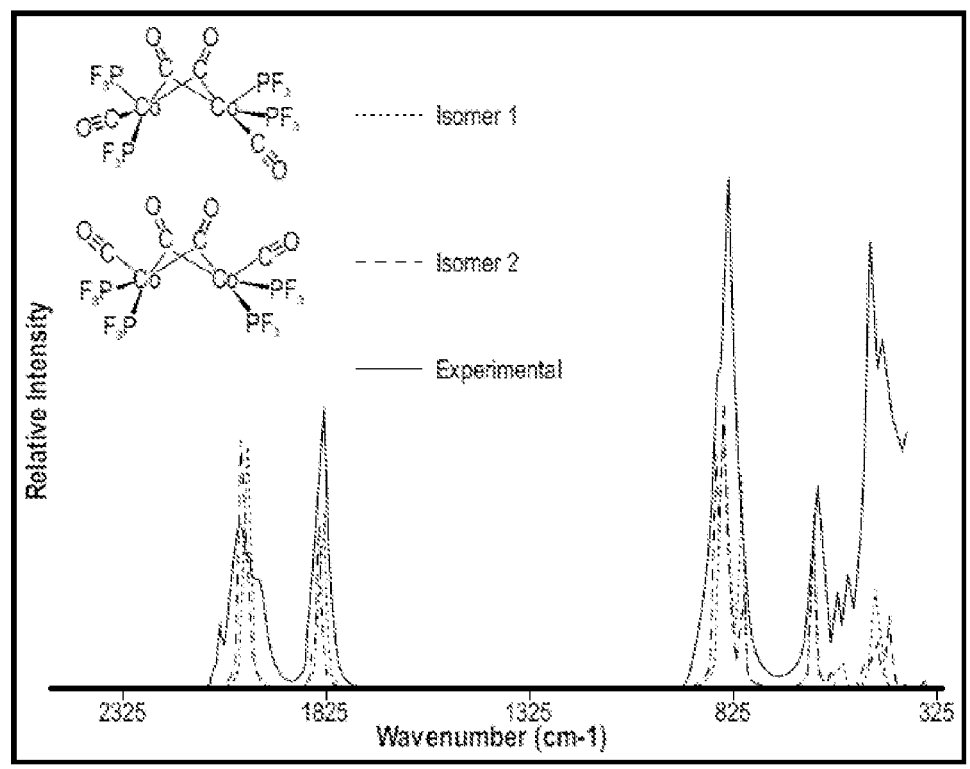
FIG. 2 shows the ATR-FTIR spectrum of the reaction product of Example 1 overlaid atop simulated IR spectra for two possible Co$_2$(CO)$_4$(PF$_3$)$_4$ isomers.

FIG. 1 shows an ATR-FTIR spectrum of the reaction product of Example 1, and FIG. 2 shows the ATR-FTIR spectrum from FIG. 1 overlaid atop simulated IR spectra for two possible Co$_2$(CO)$_4$(PF$_3$)$_4$ isomers. The ATR-FTIR spectrum of the reaction product exhibited absorbances at 2085, 2037, and 1831 cm$^{-1}$. These peaks are assigned to terminal and bridging carbonyl stretches, respectively. The high intensity stretch at 839 cm$^{-1}$ is assigned to a P-F stretch. No absorbance assignable to residual hydrocarbon solvent was observed at either 3,000 or 1,500 cm$^{-1}$. The simulated IR spectra (FIG. 2) confirmed that the experimental IR spectrum correlated well with that expected by theory. Simulated IR spectra were collected using the Amsterdam Density Function (ADF) program suite, version 2016.106. ADF was used to perform density functional theory calculations and IR simulations. For all calculations, triple-(Slater-type orbital (TZ2P) ADF basis set were utilized without frozen cores. Relativistic effects were included by use of a zeroth-order regular approximation (ZORA). The Local Density Approximation (LDA) in the exchange-and-correlation functional is ADF's implementation of that from Vosko, Wilk and Nussair (VWN). The generalized gradient approximation (GGA) employed ADF's BP86 GGA functional using that Becke (Exchange) and Perdew (Correlation). Vibration frequency calculation (IR simulations) were conducted on geometry optimized molecular structures with stable energetic minima. Simulated vibrational spectra were visualized with the ADFView graphical routine and spectra exported as XY files.

Figure 3:
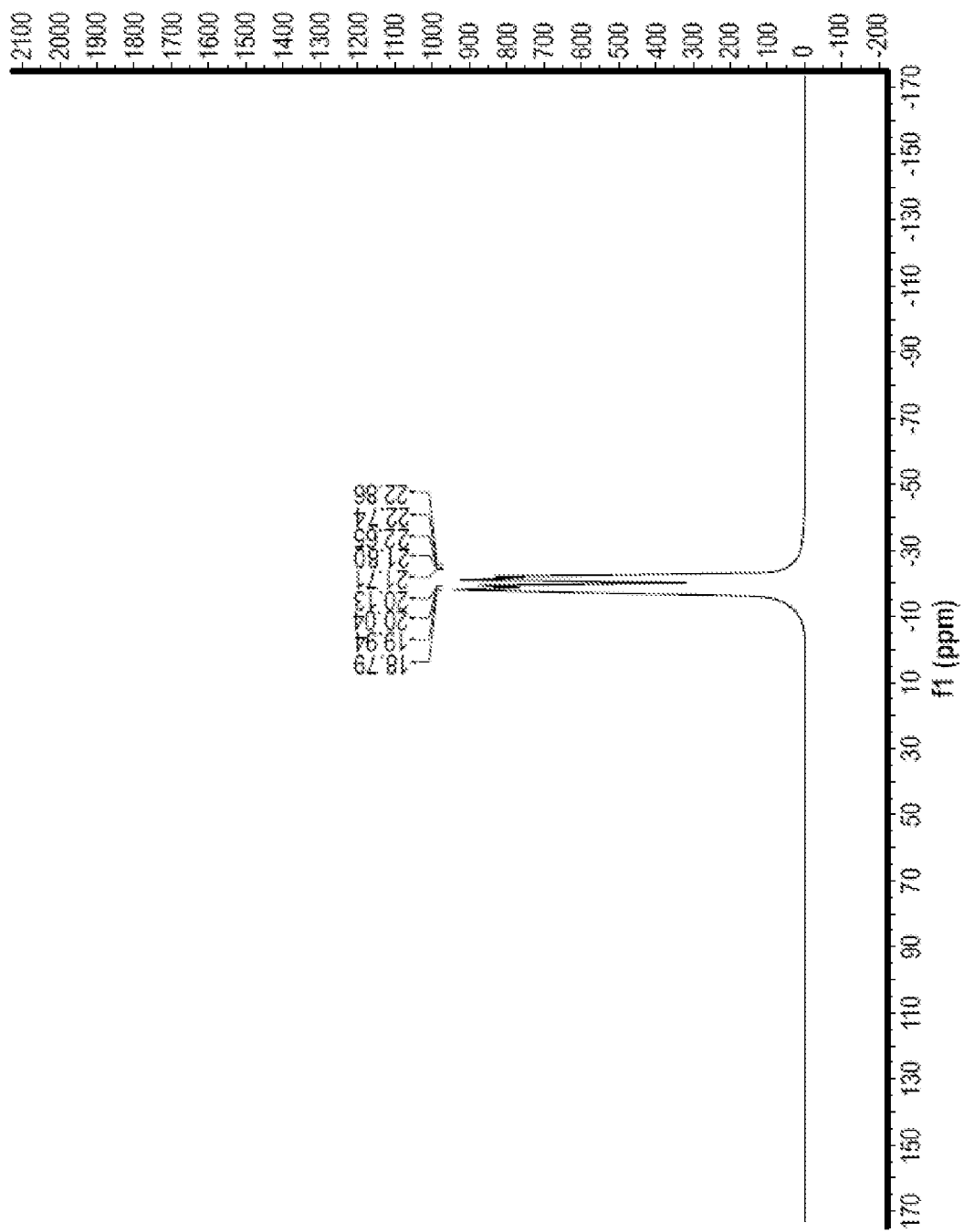
FIG. 3 shows a $^{19}$F NMR spectrum of the reaction product of Example 1.
Figure 4:
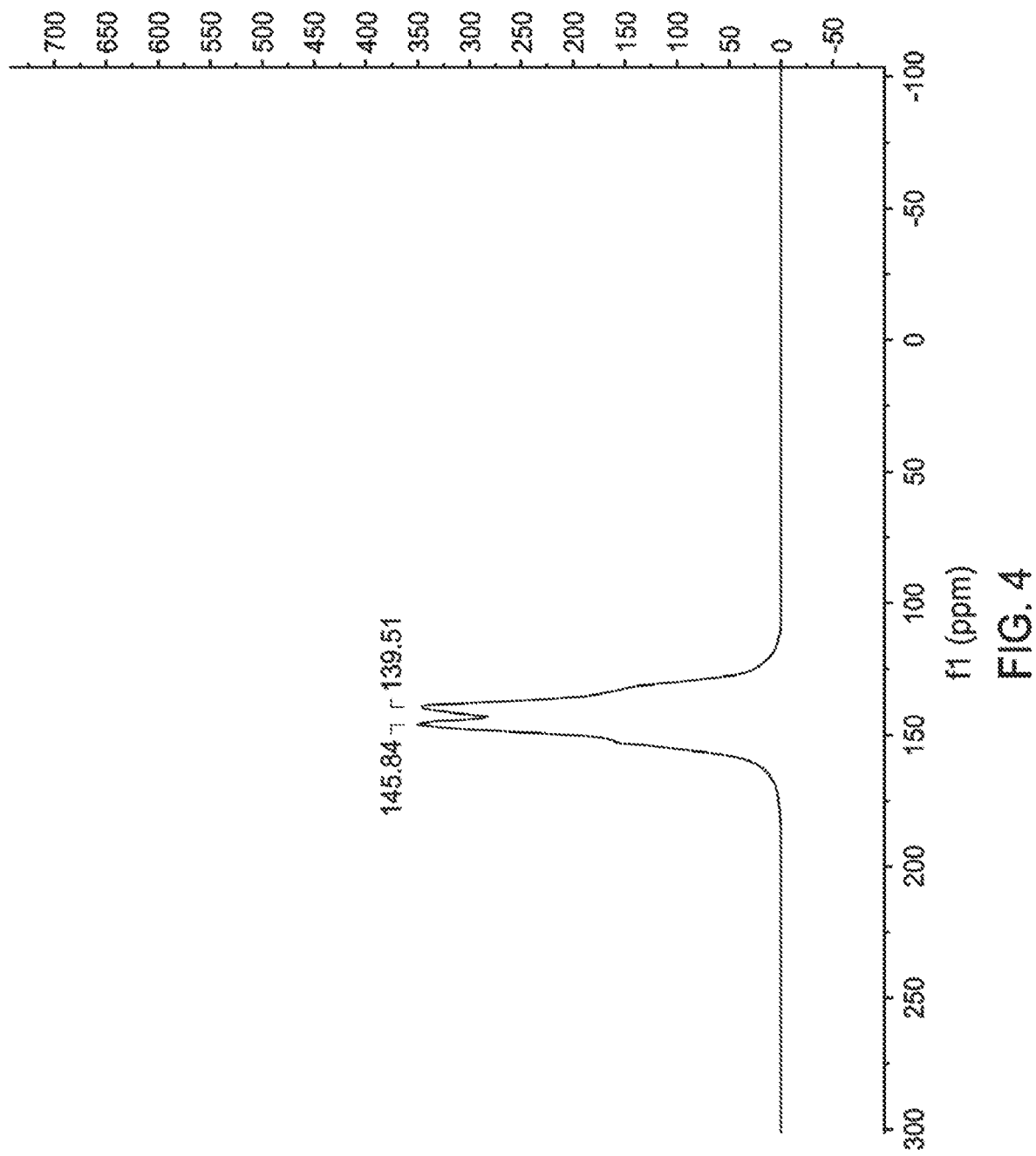
FIG. 4 shows a $^{31}$P{$^1$H} NMR spectrum of the reaction product of Example 1.
Figure 5:
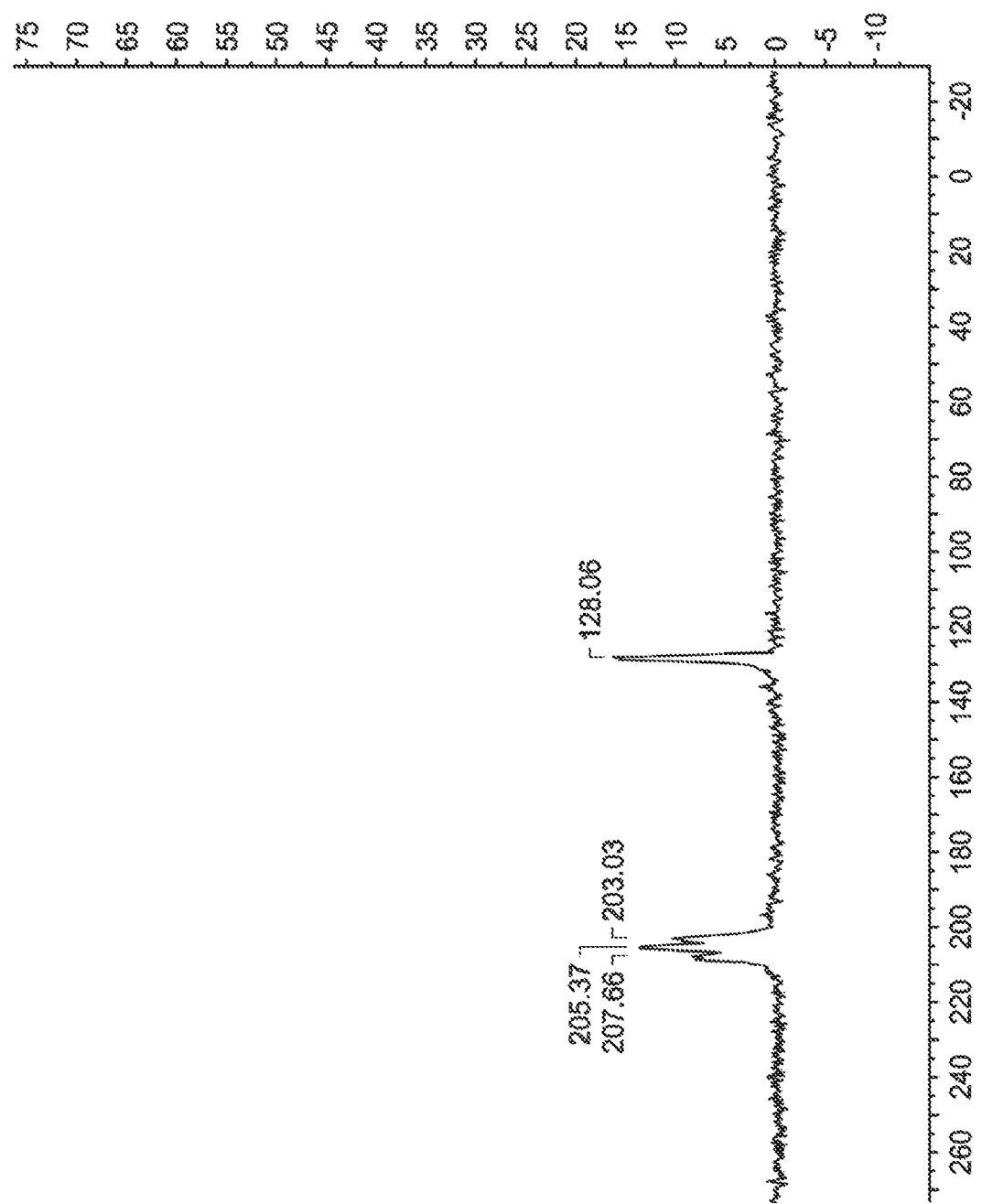
FIG. 5 shows a $^{13}$C{$^1$H} NMR spectrum of the reaction product of Example 1.

FIGS. 3-5 show $^{19}F$, $^{31}P\{^1H\}$, and $^{13}C\{^1H\}$ NMR spectra of the reaction product of Example 1. The NMR spectra were consistent with the presence of these nuclei in multiple chemical environment. All of the NMR spectra exhibited broadening consistent with coupling to $^{59}$Co (S=7/2, 100% abundant).

Example 2: Hydroformylation with 1-Hexene Feed. 1-Hexene was used as a model substrate to illustrate the product selectivity differences between hydroformylation using an unmodified cobalt catalyst precursor (Co$_2$(CO)$_8$) as compared to a trifluorophosphine-modified cobalt catalyst precursor (Example 1). As a further comparative, a conventional phosphine-modified cobalt catalyst (Co$_2$(CO)$_8$+4 equivalents of PPh$_3$) was also run under similar hydroformylation conditions. Reactions were conducted at 1,500 psig (10 MPa, 1:1 H$_2$/CO) for one hour at 150° C. with 1,500 ppm cobalt. The reaction product was analyzed by gas chromatography, and results are summarized in Table 1 below.

TABLE 1

| Entry | Catalyst | Conversion to Aldehydes and Alcohols (wt. %) | 1-Heptanal Product Selectivity (wt. %) | Aldehyde Linear-to-Branched Ratio |
|---|---|---|---|---|
| 1 | Example 1 | 39.98 | 44.77 | 0.96 |
| 2 | Co$_2$(CO)$_8$ | 88.42 | 37.28 | 0.77 |
| 3 | Co$_2$(CO)$_8$ + 4 Eq. PPh$_3$ | 18.83 | 73.22 | 2.73 |

| Entry | Catalyst Turnover Frequency (hours$^{-1}$) | Aldehyde in Product (mol. %) | Alcohol in Product (mol. %) | Paraffin in Product (mol. %) |
|---|---|---|---|---|
| 1 | 186.65 | 91.19% | 0.00% | 8.81% |
| 2 | 412.75 | 85.66% | 4.88% | 9.46% |
| 3 | 87.89 | 100.00% | 0.00% | 0.00% |

Figure 6:
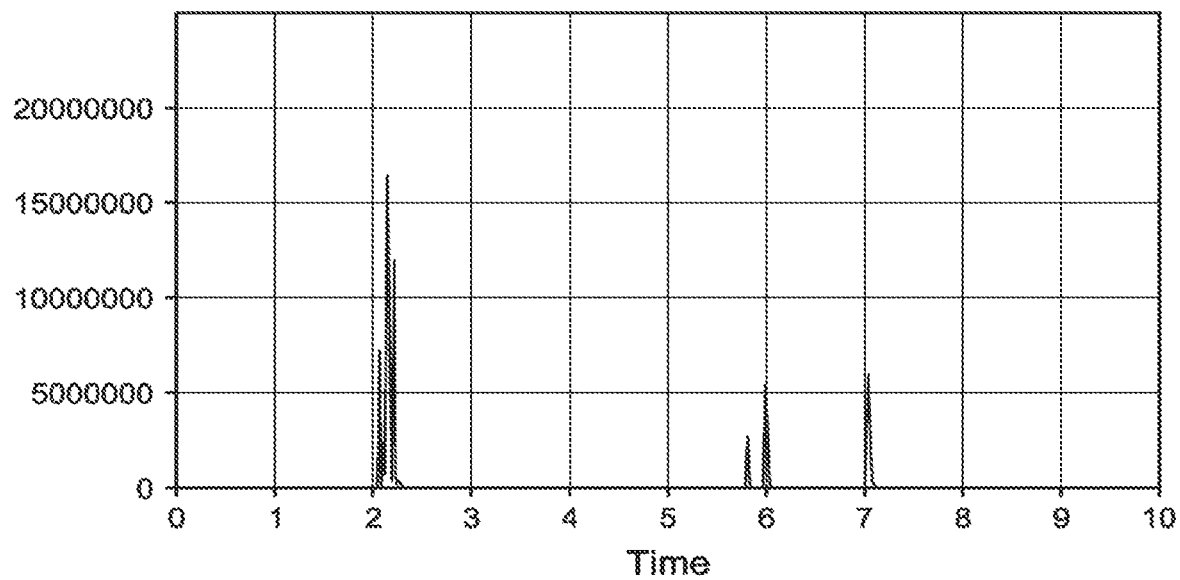
Figure 7:
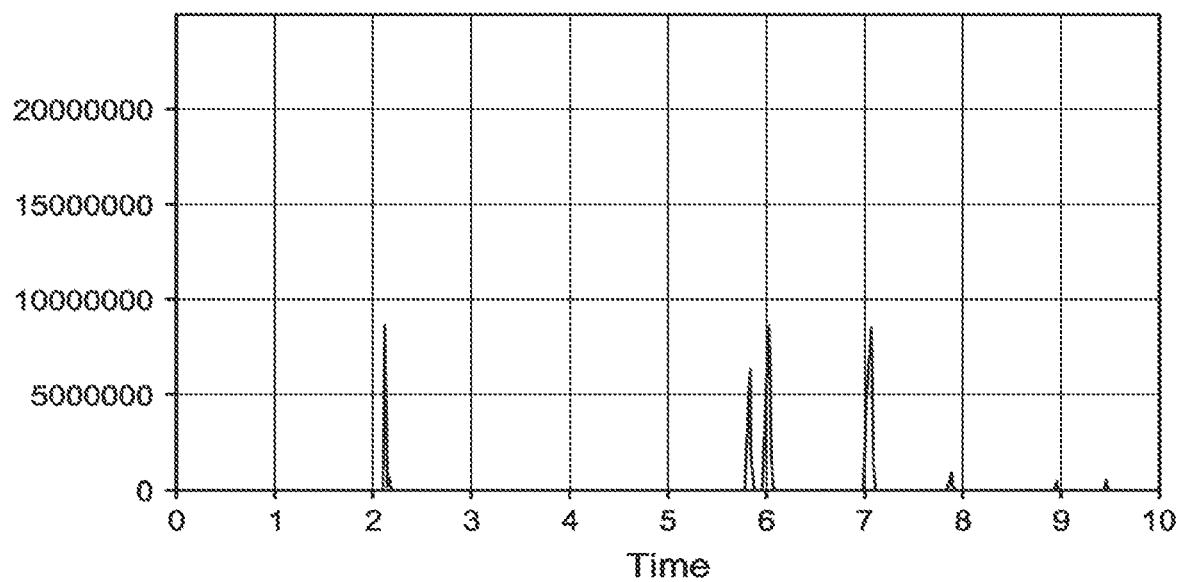

Notably, PF$_3$-modified cobalt catalysts (Entry 1) appeared substantially more active than cobalt catalysts modified with a conventional phosphine such as PPh$_3$ (Entry 3). The activity of PF$_3$ modified cobalt catalysts (Entry 1) was lower than that obtained with Co$_2$(CO)$_8$ (Entry 2), and the product distribution was considerably different. This observation suggests that PF$_3$ remains coordinated to cobalt even at elevated pressures and temperatures, in contrast to the behavior observed with conventional phosphines. FIGS. 6-8 show gas chromatographs of the product obtained from Entries 1, 2, and 3, respectively.

Notably, there was no evidence of cobalt plating observed from the run of Entry 1, whereas there was significant precipitation of a solid in the run of Entry 2, which was observable both visually and by light scattering. In the image of FIG. 9A, significant plating was observed from the run of Entry 2, whereas the image of FIG. 9B showed limited plating in the run from Entry 1.

Example 3: Hydroformylation of Complex Feed. Example 2 was repeated, except as modified in Table 2 below, using TETRAMER K (ExxonMobil, a mixture of C$_{12}$ olefinic hydrocarbons produced by oligomerizing propylene over a solid phosphoric acid catalyst and including linear alpha olefins, linear internal olefins, and highly substituted branched internal olefins (e.g., di-substituted, tri-substituted, and tetra-substituted).

TABLE 2

| Entry | Catalyst | Pressure (psi) | Conversion (%) | Turnover Frequency ($h^{-1}$) |
|---|---|---|---|---|
| 5 | Example 1 | 400 | 3.44% | 2.68 |
| 6 | Example 1 | 1500 | 21.00% | 16.35 |
| 7 | Example 1 | 1500 | 16.16% | 12.58 |
| 8 | $Co_2(CO)_8$ | 1500 | 50.92% | 79.16 |

Figure 10:
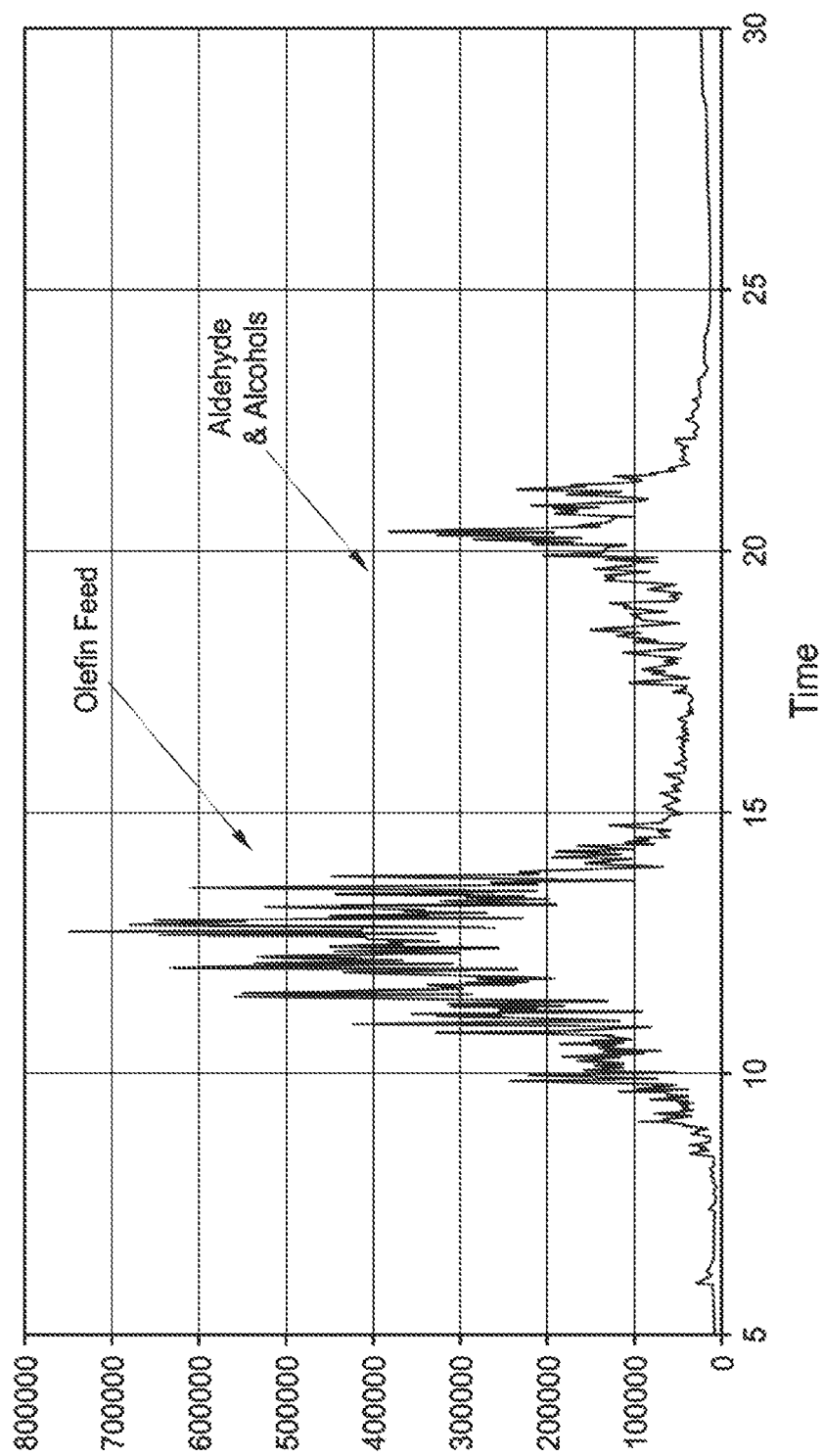
FIG. 10 shows an illustrative gas chromatograph of the hydroformylation reaction product obtained from Example 3.

Phosphine-modified cobalt hydroformylation catalysts typically react poorly with complex feeds like TETRAMER K. In contrast, the $PF_3$-modified cobalt catalyst of Example 1 exhibited good turnover frequencies and good conversion at high syngas pressures (Entries 6 and 7), albeit not at high as that observed with $Co_2(CO)_8$ (Entry 8). At a lower reaction pressure (Entry 5), the conversion and turnover frequency was much lower for the $PF_3$-modified cobalt catalyst of Example 1. FIG. 10 shows an illustrative gas chromatograph of the product obtained from Example 3.

All documents described herein are incorporated by reference herein for purposes of all jurisdictions where such practice is allowed, including any priority documents and/or testing procedures to the extent that they are not inconsistent with this text. As is apparent from the foregoing general description and the specific embodiments, while forms of the disclosure have been illustrated and described, various modifications may be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

The invention claimed is:

1. A composition comprising a compound having a formula of:

$$M_2(CO)_m(PF_3)_n;$$

wherein M is a group 9 metal, m is 1, 2, 3, 4, 5, 6, or 7, n is 1, 2, 3, 4, 5, 6, or 7, and the sum of m and n is 8.

2. The composition of claim 1, wherein M is cobalt.

3. The composition of claim 1, wherein m is 2, 3, 4, 5, 6, or 7.

4. The composition of claim 1, wherein the compound has two bridging carbon monoxide groups each between a first metal center and a second metal center.

5. The composition of claim 1, wherein the compound is represented by the formula

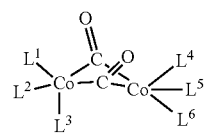

wherein $L^1$, $L^2$, $L^3$, $L^4$, $L^5$, and $L^6$ are independently CO or $PF_3$, provided that at least one of $L^1$, $L^2$ and $L^3$ is CO, at least one of $L^4$, $L^5$ and $L^6$ is CO, and at least one of $L^1$, $L^2$, $L^3$, $L^4$, $L^5$, and $L^6$ is $PF_3$.

6. The composition of claim 1, wherein m and n are each 4.

7. The composition of claim 5, wherein at least two of $L^1$, $L^2$, and $L^3$ are $PF_3$ and at least one of $L^1$, $L^2$, and $L^3$ is CO, and at least two of $L^4$, $L^5$, and $L^6$ are $PF_3$ and at least one of $L^4$, $L^5$, and $L^6$, is CO.

8. The composition of claim 1, wherein the compound is represented by one or more of the following formulas:

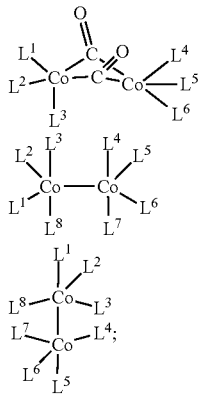

wherein, $L^1$, $L^2$, $L^3$, $L^4$, $L^5$, $L^6$, $L^7$, and $L^8$ are independently CO or $PF_3$, and if the compound is carbonyl bridged, at least one of $L^1$-$L^6$ is $PF_3$, any of $L^1$-$L^6$ that are not $PF_3$ are CO, and if the compound has a cobalt-cobalt bond, at least one of $L^1$-$L^8$ is $PF_3$ and any of $L^1$-$L^8$ that are not $PF_3$ are CO.

9. The composition of claim 1 wherein M is Rh.

10. A catalyst system comprising the reaction product of the compound of claim 1 and hydrogen.

11. The catalyst system of claim 10, wherein the catalyst system does not decompose at CO partial pressures of less than 10 MPa.

12. The catalyst system of claim 10, wherein the catalyst system does not produce hydroformylation reaction product having more group 9 metal precipitates per gram than a catalyst system consisting essentially of the reaction product of $HCo(CO)_4$ and hydrogen produces per gram, when tested under the same hydroformylation reaction conditions.

13. The catalyst system of claim 10, wherein the catalyst system is stable at temperatures of 80° C. or more and CO partial pressures of less than 10 MPa.

14. The catalyst system of claim 10, wherein the catalyst system is liquid at temperatures of 10° C. or more, and optionally at CO partial pressures of 6.9 MPa or more.

15. A method comprising contacting an olefinic hydrocarbon with the catalyst system of claim 1 under conditions effective to convert the olefinic hydrocarbon into a hydroformylation reaction product.

16. A method comprising: contacting an olefinic hydrocarbon with the composition of claim 1, hydrogen, and an oxygen source under conditions effective to convert the olefinic hydrocarbon into a hydroformylation reaction product.

17. A method comprising:
contacting an olefinic hydrocarbon with a hydrogen source and a precatalyst comprising a formula of

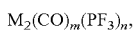

wherein the precatalyst is formed as the reaction product of $Co_2(CO)_8$ and $PF_3$ under conditions effective to convert the olefinic hydrocarbon into a hydroformylation reaction product, wherein M is a group 9 metal, at least one M is cobalt, m is 1, 2, 3, 4, 5, 6, or 7, n is 1, 2, 3, 4, 5, 6, or 7, and the sum of m and n is 8; and forming an active hydroformylation catalyst comprising a compound represented by the formula of

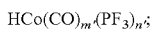

from the reaction product under the conditions effective to convert the olefinic hydrocarbon into the hydroformylation reaction product, wherein m' is 1, 2, or 3, n' is 1, 2, or 3 and the sum of m' and n' is 4.

18. The method of claim 17, wherein the contacting includes additionally contacting the olefinic hydrocarbon with an oxygen source.

19. The method of claim 15, further comprising converting the hydroformylation reaction product into a reduced hydroformylation reaction product by hydrogenating the hydroformylation reaction product.

20. The method of claim 15, wherein the conditions effective to convert the olefinic hydrocarbon into the hydroformylation reaction product comprise a combined H and O partial pressure of at least about 6.9 MPa.

21. The method of claim 15, wherein the conditions effective to convert the olefinic hydrocarbon into the hydroformylation reaction product comprise a combined H and CO partial pressure of at least about 6.9 MPa.

22. The method of claim 17, wherein m' is 2 or 3.

23. The method of claim 17, wherein m' and n' are each 2.

24. The method of claim 1, wherein the olefinic hydrocarbon comprises an alpha olefin.

25. The method of claim 23, wherein the hydroformylation reaction product has a ratio of linear aldehydes to branched aldehydes of about 0.9 to about 2.

26. The method of claim 15, wherein the olefinic hydrocarbon comprises an alpha olefin, a vinylidene olefin, a vinyl olefin, a trisubstituted olefin, a tetrasubstituted olefin, or any combination thereof.

27. The method of claim 15, wherein the olefinic hydrocarbon comprises one or more propylene oligomers.

28. A method comprising:
forming an active hydroformylation catalyst represented by the formula:

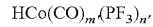

under conditions effective to convert an olefinic hydrocarbon into a hydroformylation reaction product using a precatalyst compound having a formula of:

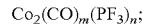

wherein m' is 1, 2, or 3, n' is 1, 2, or 3, and m'+n' is 4; wherein m is 1, 2, 3, 4, 5, 6, or 7, n is 1, 2, 3, 4, 5, 6, or 7, and the sum of m and n is 8, and contacting the olefinic hydrocarbon with the active hydroformylation catalyst and syngas under the conditions effective to convert the olefinic hydrocarbon into the hydroformylation reaction product.

29. The method of claim 28, wherein the conditions effective to convert the olefinic hydrocarbon into the hydroformylation reaction product comprise a syngas pressure of at least about 6.9 MPa.

30. The method of claim 28, further comprising: converting the hydroformylation reaction product into a reduced hydroformylation reaction product by hydrogenating the hydroformylation reaction product.

31. The method of claim 28, wherein m' is 1, 2 or 3.

32. The method of claim 28, wherein m' and n' are each 2.

33. The method of claim 28, wherein the olefinic hydrocarbon comprises an alpha olefin.

34. The method of claim 33, wherein the hydroformylation reaction product has a ratio of linear aldehydes to branched aldehydes of about 0.9 to about 2.

35. The method of claim 28, wherein the olefinic hydrocarbon comprises an alpha olefin, a vinylidene olefin, a vinyl olefin, a trisubstituted olefin, a tetrasubstituted olefin, or any combination thereof.

36. The method of claim 28, wherein the olefinic hydrocarbon comprises one or more propylene oligomers.

37. The method of claim 15, further comprising recovering the hydroformylation catalyst or a spent form thereof and conveying the recovered catalyst to an upstream location for reuse.

38. The method of claim 37 wherein the hydroformylation catalyst or a spent form thereof is recovered by vapor phase recovery.

39. The method of claim 38 wherein the vapor phase recovery utilizes CO, syngas, hydrogen, or nitrogen as a stripping gas.

* * * * *